United States Patent
Nakai et al.

(10) Patent No.: US 7,144,376 B2
(45) Date of Patent: *Dec. 5, 2006

(54) LIABLE CARDIAC MUSCLE DIAGNOSING APPARATUS AND LIABLE CARDIAC MUSCLE ANALYZING METHOD BY MAGNETIC FIELD MEASUREMENTS

(75) Inventors: Kenji Nakai, Morioka (JP); Masahito Yoshizawa, Morioka (JP); Kohei Kawazoe, Morioka (JP); Keita Yamazaki, Inzai (JP); Satoshi Fujita, Osaka (JP); Itsuro Tamura, Osaka (JP)

(73) Assignees: Japan Science and Technology Corporation, Kawaguchi (JP); Takenaka Corporation, Osaka (JP)

( * ) Notice: Subject to any disclaimer, the term of this patent is extended or adjusted under 35 U.S.C. 154(b) by 297 days.

This patent is subject to a terminal disclaimer.

(21) Appl. No.: 10/333,070
(22) PCT Filed: Jul. 17, 2001
(86) PCT No.: PCT/JP01/06193
§ 371 (c)(1), (2), (4) Date: Jun. 30, 2003
(87) PCT Pub. No.: WO02/05714
PCT Pub. Date: Jan. 24, 2002

(65) Prior Publication Data
US 2004/0039291 A1 Feb. 26, 2004

(30) Foreign Application Priority Data
Jul. 18, 2000 (JP) .............................. 2000-217834

(51) Int. Cl.
A61B 5/02 (2006.01)
(52) U.S. Cl. .................................................. 600/508
(58) Field of Classification Search ............... 600/407, 600/508–510, 518
See application file for complete search history.

(56) References Cited

U.S. PATENT DOCUMENTS

2003/0149354 A1* 8/2003 Bakharev .................... 600/407

(Continued)

FOREIGN PATENT DOCUMENTS

EP 0968683 A1 1/2000

(Continued)

OTHER PUBLICATIONS

Robinson, S.E. et al., "Functional Neuroimaging by Synthetic Aperture Magnetometry (SAM)," Proceedings of the 11th International Conference on Biomagnetism, "Recent Advances in Biomagnetism," Tohoku University Press, 1999, pp. 302-305.

(Continued)

*Primary Examiner*—George Manuel
(74) *Attorney, Agent, or Firm*—Birch, Stewart, Kolasch & Birch, LLP

(57) ABSTRACT

A magnetic field distribution measurement device (1) provides a non-contact magnetic measurement on a subject's chest at a plurality of coordinates and forms therefrom time-series magnetic field distribution data. A first arithmetic device (2) in response generates image data representing a three-dimensional, intramyocardial current density distribution. A second arithmetic device (3) receives a plurality of tomographic image data separately obtained by a tomographic diagnosis apparatus and processes the data to generate three-dimensional, anatomical image data. A display device (4) receives these data and displays on an anatomical image an image representing an intramyocardial current density. Thus in a ventricle a lesioned or viable part of myocardium can be readily identified in location, size, geometry and level. Furthermore, the anatomical image may be replaced with an image representing a normal stimulation propagation circuit and serving as a template.

11 Claims, 20 Drawing Sheets

U.S. PATENT DOCUMENTS

| | | | |
|---|---|---|---|
| 2004/0049119 A1* | 3/2004 | Nakai et al. | 600/510 |
| 2004/0077964 A1* | 4/2004 | Nakai et al. | 600/518 |
| 2005/0102013 A1* | 5/2005 | Lau | 607/129 |

FOREIGN PATENT DOCUMENTS

| | | |
|---|---|---|
| JP | 8-289877 A | 11/1996 |
| JP | 10-276998 A | 10/1998 |
| JP | 10-323335 A | 12/1998 |
| JP | 11-128191 A | 5/1999 |
| JP | 11-128224 A | 5/1999 |
| WO | WO 98/15226 A1 | 4/1998 |

OTHER PUBLICATIONS

Hara, K. et al., "Science of Cerebric Magnetic Field—SQUID Measurement and Medical Applications," Ohmsha, Jan. 25, 1997, pp. 117-119 (with partial translation).

Ueda, T. et al., "Visualization of Source Current Distribution in Human Heart based on Magnetocardiogram Data," 9th Digital Signal Processing Symposium, Nov. 10-11, 1994, pp. 307-312.

* cited by examiner

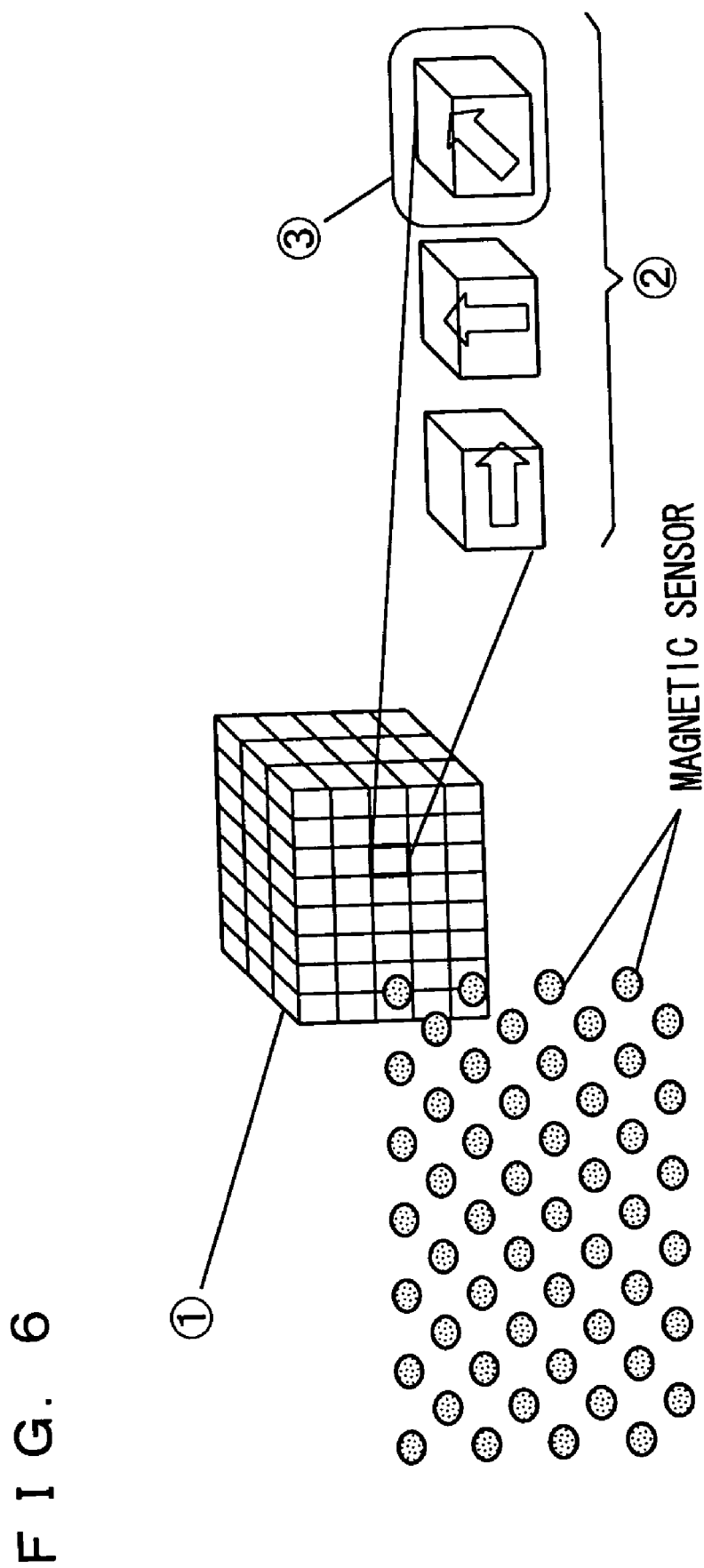

LIABLE CARDIAC MUSCLE DIAGNOSING APPARATUS AND LIABLE CARDIAC MUSCLE ANALYZING METHOD BY MAGNETIC FIELD MEASUREMENTS

This application is the national phase under 35 U.S.C. § 371 of PCT International Application No. PCT/JP01/06193 which has an International filing date of Jul. 17, 2001, which designated the United States of America.

1. Technical Field

The present invention relates generally to viable myocardium diagnosis apparatuses and analysis methods employing a magnetic measurement and particularly to those employing a non-contact magnetic measurement to non-invasively identify a lesioned part of myocardium that might cause an oscillation loop (a reentry circuit) of an abnormal electric current in right and left ventricles or a viable part of myocardium.

2. Background Art

Conventionally, electrocardiograms has been generally adopted as a technique to diagnose heart diseases.

However, conventional electrocardiography is insufficient for example to determine the location, size and geometry of a lesioned or viable part of myocardium prior to heart surgeries.

This is attributed to the fact that electrocardiography is an indirect measurement methodology. Different subjects have different tissues existing between their hearts and body surfaces, different positional relationships between their hearts and other organs and bones, their respective hearts having different sizes, a different electric conductance for each tissue of their bodies, and the like. As such, it has been significantly difficult to accurately determine an affected part from information obtained from electrocardiography.

If a part of myocardium that is lesioned from ischemia and a part of myocardium that is physiologically viable (hereinafter referred to as "viable myocardium") coexist in a ventricle, an electrically abnormal reentry circuit may be formed in myocardium and for example cause ventricular tachycardia. Accordingly there exist a strong demand for accurately, three-dimensionally identifying such a lesioned or viable part of myocardium.

Electrocardiography is useful in diagnosing whether myocardium has a part lesioned from ischemia. However, it would hardly be so in recognizing the location, size and geometry of a lesioned part of myocardium in a heart.

In recent years, magnetic resonance imaging (MRI), x-ray CT and other medical, tomography apparatuses have prevailed rapidly. They are useful in examining an anatomical structure of the cardiovascular system with high precision. However, they can hardly be used to recognize the location, size and geometry of lesioned and viable parts of myocardium.

Accordingly, medical institutions currently evaluate viable myocardium using myocardial SPECT, PET or any other similar tests employing a radioactive isotope. Furthermore, evaluating a property of a myocardial tissue entails an invasive test methodology directly obtaining a tissue for example using a catheter or performing a surgical operation to sample a myocardial tissue (biopsy of myocardium).

Of these techniques, myocardial SPECT, PET or other similar test methodologies using a radioactive isotope is used as a method for accurately evaluating a survival condition of myocardium before and after angina pectoris following myocardial infarction, or a coronary bypass graft operation. These test methodologies, however, use a radioactive isotope. Accordingly, employing them in a controlled area is obligatory and also expensive.

Furthermore, making a decision after a heart transplant as to whether a treatment is necessary in accordance with the level of a rejection also requires evaluating rejected myocardium, and in addition requires conducting a test at relatively small intervals chronologically a number of times to see whether a rejection is present or absent. Test methodologies employing electrocardiography, echocardiography or the like can be employed to capture a variation of a myocardial rejection. However, they do not have a precision necessary for diagnosis, i.e., as high a precision as necessary for determining the level of a rejection, Accordingly after heart transplants a catheter is used to regularly conduct myocardial biopsy, which is a significant invasive on patients. Accordingly there has been a strong demand for an apparatus capable of employing a non-invasive measurement means to three-dimensionally diagnose the location, size and level of a rejected myocardium after heart transplants.

In a variety of fields a superconducting quantum interference device (SQUID) magnetometer has been applied. It uses an SQUID capable of detecting with high sensitivity a magnetic flux of one billionth of geomagnetism. In particular, in the field of somatometry, which strongly demands non-invasive measurement, as described above, an attempt is being made to use a SQUID magnetometer to provide a non-contact magnetic measurement of human bodies.

In particular, the development of thin-film device fabrication technology in recent years has allowed the development of a DC-SQUID, and an attempt is being made to use a SQUID magnetometer to measure a magnetocardiogram, a distribution of a magnetic field of a heart.

However, a magnetocardiogram alone cannot directly display the location, size, geometry and level of a lesioned or viable part of myocardium in a human body and hardly allows doctors to correctly understand a relative, positional relationship of an affected part in a heart.

Accordingly it has been proposed to visualize an intramyocardial, electric current behavior from a magnetocardiographically represented cardiomagnetic field distribution. One such approach adopted is to use one or more current dipoles to mimic the source of a magnetic field for visualization. However, the entirety of myocardium is electrically active with a spread. As such, substituting the entirety of myocardium with a single electric-current vector cannot provide current density information indicating myocardium's electrophysiological activity and accordingly it cannot be used to identify the size and geometry of a lesioned or viable part of myocardium.

The present invention therefore contemplates a viable-myocardium diagnosis apparatus and analysis method employing a magnetic measurement, capable of employing a non-invasive magnetic measurement to obtain data representing an intramyocardial current density distribution and used to three-dimensionally identify a lesioned or viable part of myocardium safely, rapidly and with high precision.

DISCLOSURE OF THE INVENTION

In accordance with the present invention an apparatus employing a magnetic measurement to diagnose viable myocardium includes a magnetic field distribution measurement device, a first arithmetic device, a second arithmetic device and a display device. The magnetic field distribution measurement device performs a non-contact magnetic measurement on a subject's chest at a plurality of coordinates to obtain a plurality of time-series magnetic data corresponding to the plurality of coordinates, and also uses the plurality of time-series magnetic data to generate time-series magnetic field distribution data on the chest. The first arithmetic device uses the generated time-series magnetic field distribution data to generate time-series, intramyocardial current density distribution data of the subject. The second arithmetic device processes separately provided, tomographic, thoracic data of the subject to generate data representative of an anatomical image. The display device displays an image of the intramyocardial current density distribution represented by the data generated by the first arithmetic device, as superimposed on the anatomical image represented by the data generated by the second arithmetic device. Thus a lesioned part of myocardium presenting an abnormal current density distribution or a physiologically viable part of myocardium can be identified three-dimensionally.

Preferably the first arithmetic device operates based on an anatomical or functional factor to divide right and left ventricles into any plurality of regions and generates time-series data of an intramyocardial current density distribution for each the region to allow a lesioned part of myocardium in the right and left ventricles to be three-dimensionally identified.

More preferably the apparatus further includes a database containing information used to determine a relationship between an intramyocardial current density represented by data generated by the first arithmetic device and a myocardial lesion current.

In accordance with the present invention in another aspect an apparatus employing a magnetic measurement to diagnose viable myocardium includes a magnetic field distribution measurement device, an arithmetic device and a display device. The magnetic field distribution measurement device performs a non-contact magnetic measurement on a subject's chest at a plurality of coordinates to obtain a plurality of time-series magnetic data corresponding to the plurality of coordinates, and also uses the plurality of time-series magnetic data to generate time-series magnetic field distribution data on the chest. The arithmetic device uses the generated time-series, magnetic field distribution data to generate time-series, intramyocardial current density distribution data of the subject. The display device uses the data generated by the arithmetic device to superimpose together an image representing a stimulation propagation path of the subject extending from a sinoatrial node to a bundle of His-Purkinje fiber network and an image representing an intramyocardial current density distribution and displays the images. Thus a lesioned part of myocardium presenting an abnormal current density distribution or a physiologically viable part of myocardium can be three-dimensionally identified.

Preferably the arithmetic device operates based on an anatomical or functional factor to divide right and left ventricles into any plurality of regions and generate time-series data of an intramyocardial current density distribution for each the region to allow a lesioned part of myocardium in the right and left ventricles to be three-dimensionally identified.

More preferably the apparatus further includes a database containing information used to determine a relationship between an intramyocardial current density represented by data generated by the arithmetic device and a myocardial lesion current.

In accordance with the present invention in another aspect a method employing a magnetic measurement to analyze viable myocardium includes the steps of: performing a non-contact magnetic measurement on a subject's chest at a plurality of coordinates to obtain a plurality of time-series magnetic data corresponding to the plurality of coordinates and used to generate time-series, magnetic field distribution data of the chest and generating first data corresponding to time-series, intramyocardial current density distribution data of the subject from the generated time-series magnetic field distribution data; processing separately fed, tomographic, thoracic image data of the subject to generate second data representative of an anatomical image; and displaying an image of the intramyocardial current density distribution represented by the first data, as superimposed on the anatomical image represented by the second data, to allow three-dimensional identification of a lesioned part of myocardium presenting an abnormal current density distribution or a physiologically viable part of myocardium.

Preferably the step of generating the first data divides right and left ventricles into any plurality of regions based on an anatomical or functional factor and generate time-series data of an intramyocardial current density distribution for each the region to allow a lesioned part of myocardium in the right and left ventricles to be three-dimensionally identified.

More preferably the method further includes the step of determining from information indicating a relationship between an intramyocardial current density represented by the first data and a myocardial lesion current whether the three-dimensionally identified part is a lesioned or viable part of myocardium.

In accordance with the present invention in still another aspect a method employing a magnetic measurement to analyze viable myocardium includes the steps of: performing a non-contact magnetic measurement on a subject's chest at a plurality of coordinates to obtain a plurality of time-series magnetic data corresponding to the plurality of coordinates and used to generate time-series magnetic field distribution data of the chest and generating time-series, intramyocardial current density distribution data of the subject from the generated time-series magnetic field distribution data; and using the generated data to superimpose together an image representing a stimulation propagation path of the subject extending from a sinoatrial node to a bundle of His-Purkinje fiber network and an image representing an intramyocardial current density distribution and displaying the images to allow three-dimensional identification of a lesioned part of myocardium presenting an abnormal current density distribution or a physiologically viable part of myocardium.

Preferably the step of generating data divides right and left ventricles into any plurality of regions based on an anatomical or functional factor and generate time-series data of an intramyocardial current density distribution for each the region to allow a lesioned part of myocardium in the right and left ventricles to be three-dimensionally identified.

More preferably the method further includes the step of determining from information indicating a relationship between an intramyocardial current density represented by the data and a myocardial lesion current whether the three-dimensionally identified part is a lesioned or viable part of myocardium.

Thus in accordance with the present invention an image representing an intramyocardial current density distribution obtained through a non-invasive magnetic measurement that is superimposed on an anatomical image obtained by processing tomographic, thoracic image data of the same subject undergoing tomography with a separate, medical diagnosis apparatus can be displayed to allow doctors to safely, rapidly and with high precision, and three-dimensionally identify a lesioned part of myocardium presenting an abnormal current density distribution or a physiologically viable part of myocardium.

Furthermore in accordance with the present invention an image representing an intramyocardial current density distribution obtained through a non-invasive magnetic measurement that is superimposed on an image representing a stimulation propagation path of the same subject extending from an atrioventricular node to a bundle of His-a Purkinje fiber network can be displayed to allow doctors to safely, rapidly and with high precision, and three-dimensionally identify a lesioned part of myocardium presenting an abnormal current density distribution or a physiologically viable part of myocardium.

BRIEF DESCRIPTION OF THE DRAWINGS

In the drawings:

FIG. 6 schematically illustrates a method of calculating current density data from time-series magnetic data;

BEST MODE FOR CARRYING OUT THE INVENTION

Figure 1:
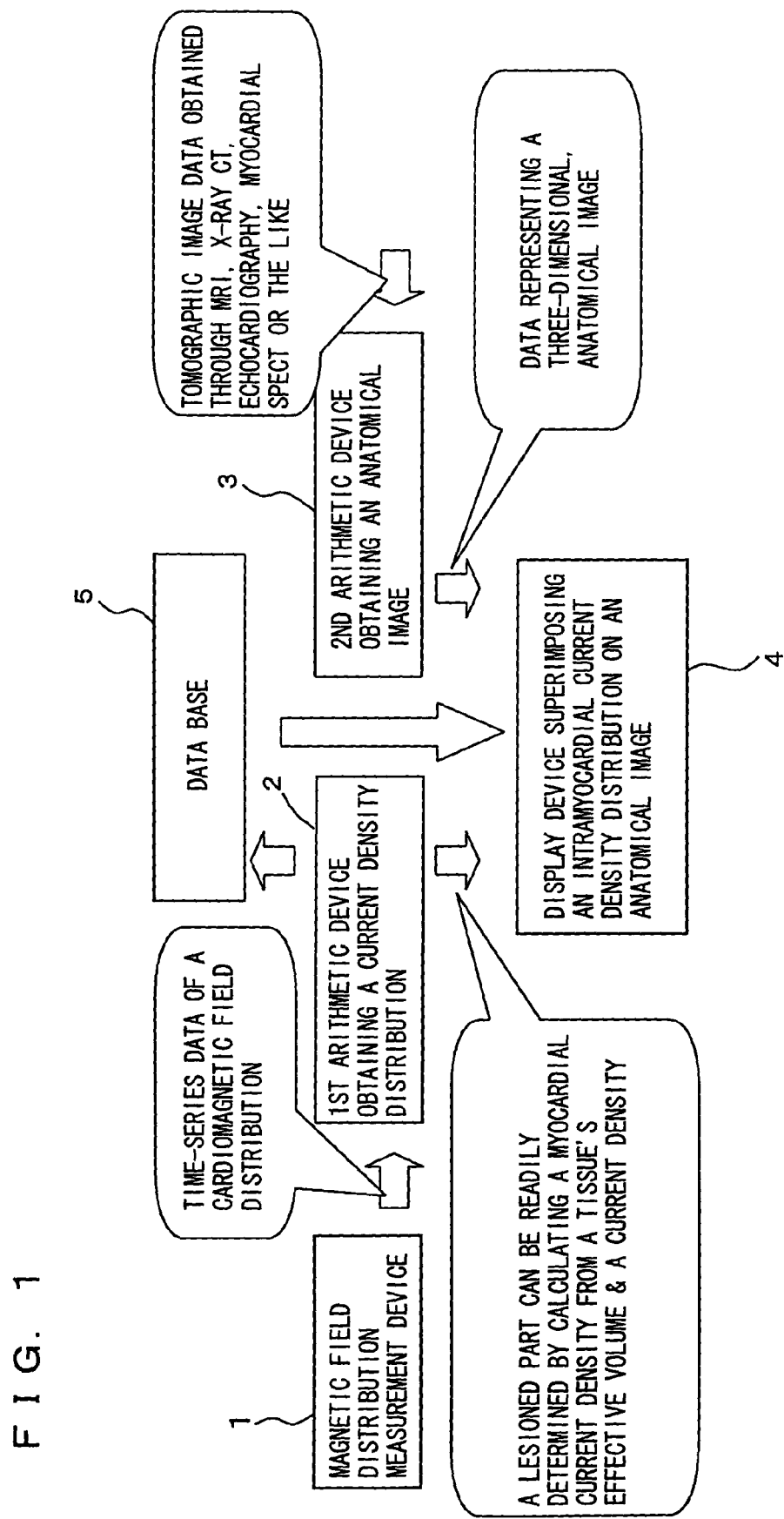
FIG. 1 is a functional block diagram schematically showing a configuration of an apparatus employing a magnetic measurement to diagnose viable myocardium in accordance with the present invention in a first embodiment.

Hereinafter, the present invention in embodiments will specifically be described with reference to the drawings. Note that in the figures, like components are denoted by like reference characters and their descriptions will not be repeated.

First Embodiment

FIG. 1 is a functional block diagram schematically showing a configuration of an apparatus in accordance the present invention in a first embodiment employing a magnetic measurement to diagnose viable myocardium.

As shown in FIG. 1, a magnetic field distribution measurement device 1 for example uses a measurement means such as a SQUID magnetometer, as will be described hereinafter more specifically, to provide a non-contact magnetic measurement on a subject's chest at a plurality of coordinates to obtain a plurality of time-series magnetic data corresponding to the plurality of coordinates. The plurality of time-series magnetic data are then used to generate and output time-series magnetic field distribution data of a magnetic field existing on the subject's chest, i.e., of the subject's heart.

The cardiac, time-series magnetic field distribution data provided by magnetic field distribution measurement device 1 is used by a first arithmetic device 2 for example employing a variety of known calculation methodologies, described hereinafter, to generate and output first data corresponding to time-series, intramyocardial current density distribution data.

Furthermore, magnetic resonance imaging (MRI), x-ray, computed tomography (CT), echocardiography, myocardial single photon emission computed tomography (SPECT) or any other similar tomographic diagnosis apparatus is used to separately obtain tomographic, thoracic image data (including data of a plurality of tomographic images) of the same subject. The data are fed to a second arithmetic device 3 and processed thereby to generate and output second data representing a three-dimensional, anatomical image.

The first data is represented in an image. By noting a tone of an image representing a current density distribution, a lesioned part of myocardium that indicates an abnormal current density or a viable part of myocardium can be three-dimensionally identified.

Display device 4 superimposes an image representing the intramyocardial current density distribution represented by the first data generated by the first arithmetic device, on a three-dimensional, anatomical image of a subject's chest that is represented by the second data generated by the second arithmetic device 3, and displays the same. As a result on an anatomical image a lesioned or viable part of myocardium can be identified three-dimensionally.

Note that display device 4 displays only the exact intramyocardial current density distribution. Accordingly, a database 5 containing information used to determine a relationship between an intramyocardial current density distribution and a myocardial lesion current is provided and a current density distribution calculated by the first arithmetic device 2 is compared with the information in database 5 and a result thereof is displayed on display device 4 to allow a decision to be more accurately made as to whether the part having the current density of interest is lesioned myocardium (for example an ischemic part of myocardium, a rejected myocardium and the like) or viable myocardium.

Figure 2:
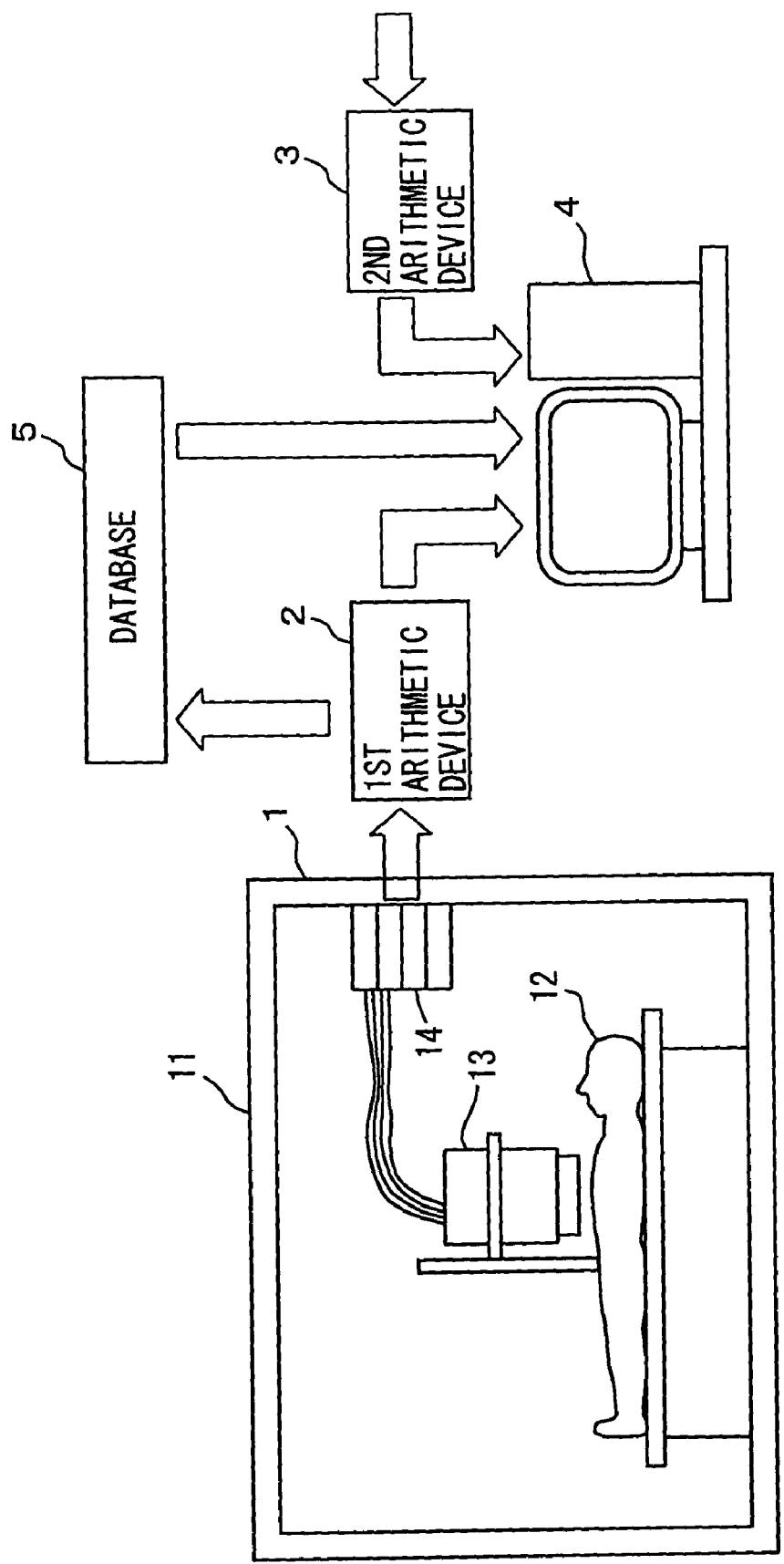
FIG. 2 is a block diagram more specifically showing the configuration of the FIG. 1 apparatus.

FIG. 2 is a block diagram more specifically showing the configuration of the apparatus employing a magnetic measurement to diagnose viable myocardium in accordance with the first embodiment shown in FIG. 1.

As shown in FIG. 2, magnetic field distribution measurement device 1 includes in a magnetic shield room (MSR) 11 a Dewar structure 13 incorporating a SQUID magnetometer and arranged on the chest of a subject 12 to provide a non-contact magnetic measurement, and a magnetic field distribution data operation unit 14.

In Dewar structure 13 is provided a low-temperature environment filled with liquid helium to provide superconductance, and in the environment is accommodated a SQUID magnetometer configured of a detector coil formed of superconductor.

Figure 3:
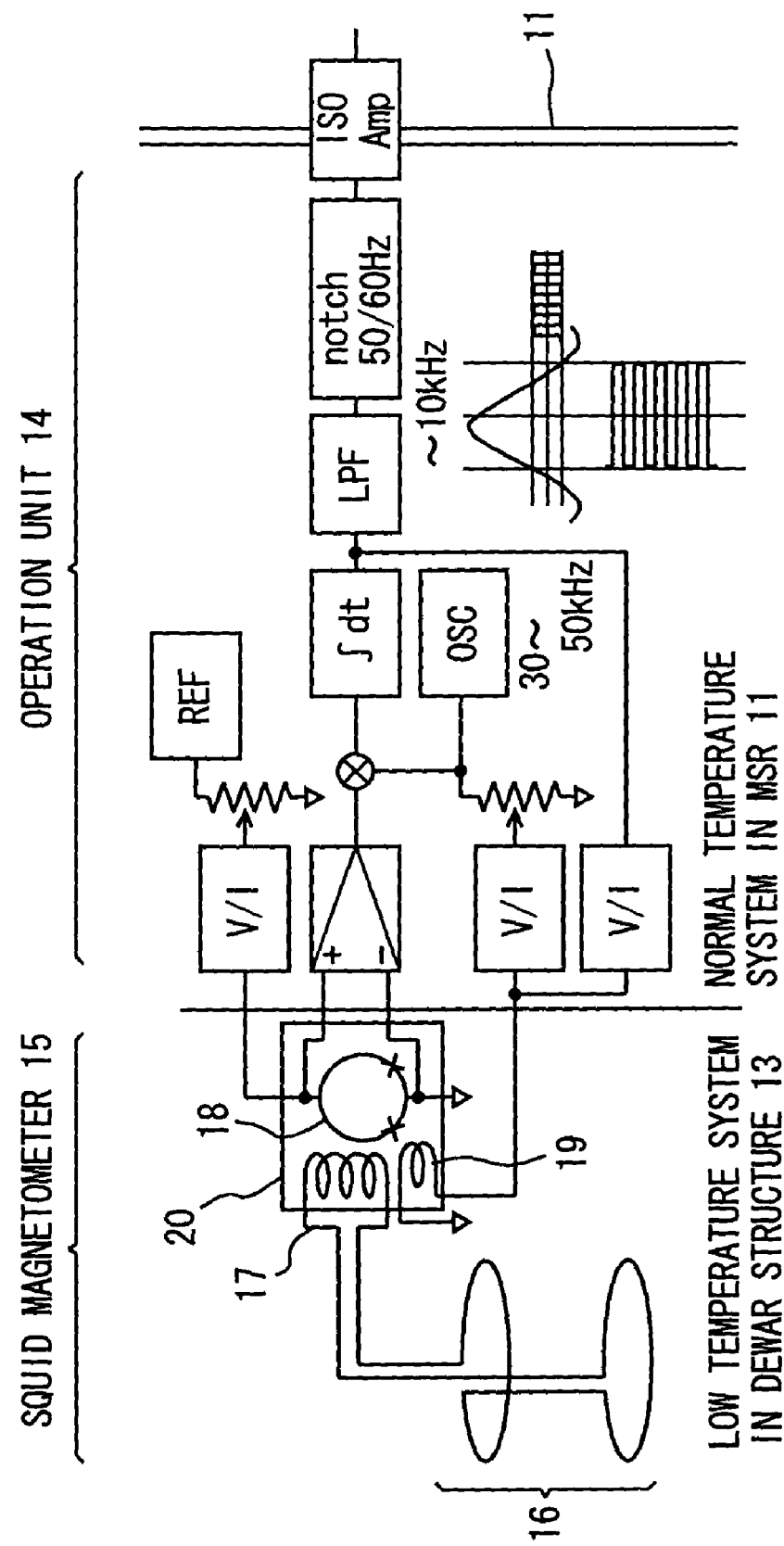
FIG. 3 is a block diagram showing a specific configuration of the magnetic field distribution measurement device shown in FIG. 2.

FIG. 3 is a block diagram more specifically showing a SQUID magnetometer 15 arranged in an ultra low temperature system provided in Dewar structure 13 arranged in MSR 11 shown in FIG. 2, and operation unit 14 arranged in MSR 11 of a normal temperature system.

Note that the configuration shown in FIG. 3 is that for a single channel for measuring magnetic data of a single point on a subject's chest. As will be described hereinafter, in the present invention, on a subject's chest at a plurality of coordinates a magnetic field is measured, i.e., a multi-point, simultaneous magnetic measurement is provided. Accordingly, MSR 11 of FIG. 2 would have therein the 1-channel configuration of FIG. 3 for each of channels required for a measurement.

With reference to FIG. 3, for a single channel a SQUID magnetometer generates magnetic data, as described hereinafter.

SQUID magnetometer 15 includes a pickup coil 16 formed of superconductor for detecting a magnetic field generated from a surface of the chest of a subject. When pickup coil 16 captures a magnetic field, a current flows and drawn in by a coil 17 to create a magnetic field in an Nb shield 20.

Consequently, a magnetic field varying linearly relative to that created in Nb shield 20 is formed in a superconducting loop 18. Voltages of opposite ends of superconducting loop 18 are detected by an amplifier of operation unit 14 provided in MSR 11 of the normal temperature system. Operation unit 14 adjusts a current flowing through a modulation coil 19 provided in Nb shield 20 so that a detected voltage can thus be free of variation.

More specifically, the detection of an electric field of a human body by a SQUID is not a direct measurement of a magnetic field generated. Rather, a so-called a zeropotential method is used to provide a feedback to allow a magnetic field in superconducting loop 18 to have a constant value (more specifically, a current flowing through modulation coil 19 is adjusted to control a magnetic field generated in modulation coil 19 so that superconducting loop 18 internally, constantly has a constant magnetic field) to allow operation unit 14 to convert to an electrical signal a magnetic field detected at pickup coil 16 and output the signal. Such a feedback technique is typically a well known technique referred to as a flux locked loop (FLL).

Such a SQUID magnetometer 15 and its operation unit 14 are well known and will not further be described.

As has been described previously, the configuration shown in FIG. 3 is that necessary for measuring magnetic data for a single channel and outputs an electrical signal corresponding to time-series magnetic data of a magnetic field measured on a front side of the chest of a subject at a single point.

In the present invention, as has been described previously, a large number of sensors (SQUID magnetometers) are arranged on a front side of the chest of a subject to measure a magnetic field on the front side at multiple points. A magnetic field varies with time and for example even during a period corresponding to a single heart beat a magnetic field that is measured at different sites exhibits different variations depending on the sites.

Figure 4:
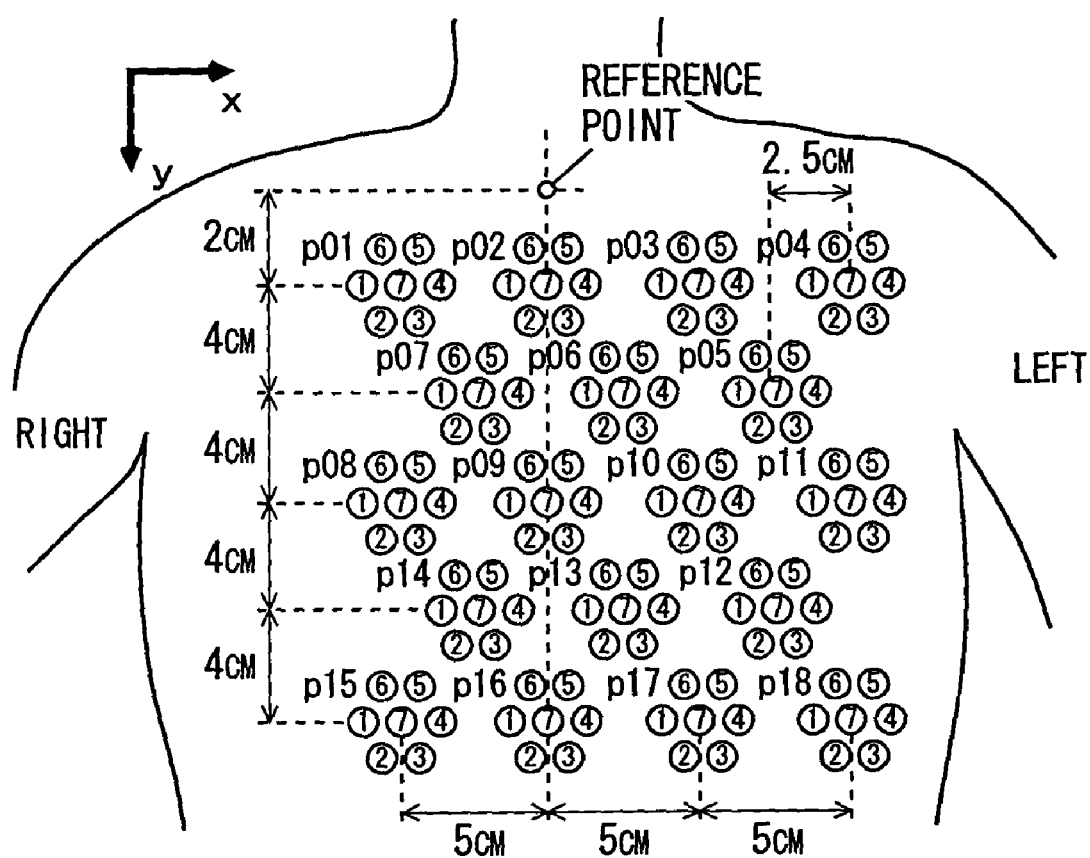
FIG. 4 shows by way of example an arrangement of a plurality of magnetic sensors on a front side of the chest of a subject.

FIG. 4 exemplarily shows an arrangement of a plurality of sensors (each corresponding to a SQUID magnetometer of a single channel) on a front side of the chest of a subject. Furthermore, FIG. 5 represents a group of time-series magnetic data representing a variation of a magnetic field for the period of a single heart beat that is obtained from the respective sensors of FIG. 4, as corresponding to their respective positions.

Figure 5:
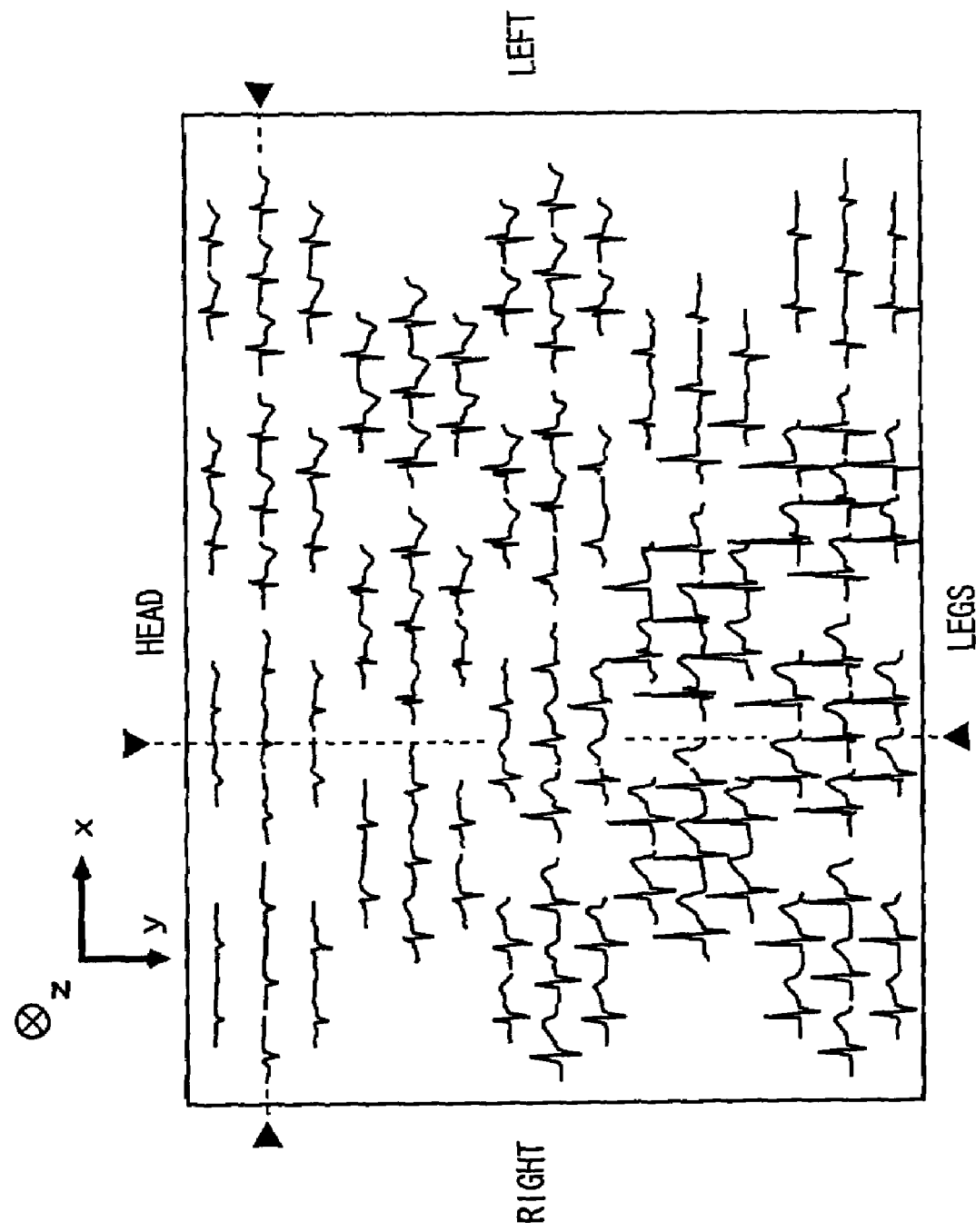
FIG. 5 represents time-series magnetic data obtained from the plurality of sensors shown in FIG. 4, respectively.

Magnetic field distribution measurement device 1 shown in FIG. 2 outputs a group of time-series magnetic data corresponding to a plurality of positions (coordinates) for measurement, as shown in FIG. 5. If a group of time-series magnetic data is captured with a particular time noted, it is difficult to graphically (diagrammatically) represent ridges and troughs representing a distribution in intensity of a magnetic field present at a specific time on a front side of a chest to be measured, and magnetic field distribution data represented in a contour map such as an atmospheric pressure represented in a weather chart is accordingly obtained. In this sense also, data output from magnetic field distribution measurement device 1 can be captured as time-series data of a distribution of a magnetic field on a front side of a chest.

A group of time-series, magnetic data such as output from magnetic field distribution measurement device 1, i.e., time-series magnetic field distribution data are fed to the first arithmetic device 2 of FIG. 2. The first arithmetic device 2 functions to obtain from magnetic field distribution data of a specific time a density of an electric current in the chest that flows at that instant.

From the time-series magnetic field distribution data generated by magnetic field distribution measurement device 1 the first arithmetic device 2 obtains a distribution of a density of a current flowing in a human body through a part to be measured (a heart in the present invention), as described hereinafter.

FIG. 6 schematically illustrates a method of obtaining a current density. The method described hereinafter is intended to indirectly calculate a current that should flow through a virtual current sensor arranged at a specific single part of a human body to be analyzed. All of sensors (SQUID magnetometers) on the chest of a human body provide time-series magnetic data, which can be multiplied by a coefficient and then added together to obtain an output of a current of the virtual sensor of interest. How the coefficient is obtained is a central issue in this arithmetic operation.

Hereinafter with reference to FIG. 6 a technique used to obtain a current density will be described more specifically. Initially on a surface of a human body (a front side of the chest thereof) there are arranged N magnetic sensors in total for the sake of illustration. As indicated by a circled number of 1, a human body (a chest, a heart in particular) to be analyzed is regarded as a collection of voxels, each in the form of a small block. There are provided M voxels in total for the sake of illustration. As indicated by a circled number of 2, at a single coordinate there is arranged a voxel passing a distribution current of mutually orthogonal components, although a component orthogonal to a plane, as indicated by a circled number of 3, is often omitted, since in magnetocardiography a magnetic sensor is often arranged on a chest in a plane.

$B_j(t)$ represents time-series magnetic data obtained from each sensor j and $\beta_{ij}$ represents a spatial filter factor of a voxel i corresponding to each sensor output $B_j(t)$.

If it is assumed that in voxel i there exist a virtual current sensor and $S_i(t)$ represents a virtual sensor output corresponding to a current density obtained from the virtual current sensor then $S_i(t)$ is defined by the following expression:

$$Si(t) = \sum_{j=1}^{N} \beta_{ij} \cdot B_j(t).$$

As such, if a spatial filter factor $\beta_{ij}$ is determined a current density in each voxel i can be obtained and a three-dimensional current density distribution can be obtained for the entirety of a subject to be analyzed.

Spatial filter factor $\beta_{ij}$ that is highly sensitive only to a distribution current of corresponding voxel i can be set by synthetic aperture magnetometry (SAM), multiple signal classification (MUSIC) or other similar, various techniques. SAM and MUSIC have been studied and developed for example in the fields of radar and sonar and are well known techniques. However, they have hitherto been unapplied to cardiomagnetism diagnosis.

A virtual sensor output of each voxel that is calculated in real time using a spatial filter factor obtained by SAM, MUSIC or any other similar technique, is an advantageously highly implemented real-time output.

SAM and MUSIC are well known techniques and the algorithms using these techniques to obtain a spatial filter factor are significantly complicated, and they will not be described specifically. SAM is specifically described by Robinson SE and Vrba J, *"Functional Neuroimaging by Synthetic Aperture Magnetometry (SAM)"* in Proceedings of the 11th International Conference on Biomagnetism, *"Recent Advances in Biomagnetism,"* published by Tohoku University Press, 1999, pp. 302–305. MUSIC is specifically described by Hiroshi Hara and Shinya Kurishiro, *"Science of Cerebric Magnetism-SQUID Measurement and Medical Applications,"* published by Ohmsha, Jan. 25, 1997, pp. 117–119.

Thus the first arithmetic device 2 generates from magnetic field distribution data generated by magnetic field distribution measurement device 1 time-series data representing a three-dimensional current density distribution in a heart to be analyzed and feeds the time-series data to display device 4 at one input.

The second arithmetic device 3 shown in FIG. 2 receives image data of a plurality of sliced images (for example a dozen of such images obtained at a pitch of five millimeters) of the chest of the same subject that are previously taken using another tomographic analysis apparatus (not shown) such as MRI, x-ray CT, echocardiography or myocardial SPECT with an electrocardiography synchronization trigger applied.

The second arithmetic device 3 processes (interpolates) the data of the plurality of sliced images and subjects the data to three-dimensional, perspective conversion from a predetermined point of view to generate second data representing an anatomical image. Thus forming a three-dimensional, anatomical image from a plurality of sliced images is a well-known technique, for example as specifically disclosed in Japanese Patent Laying-Open No. 11-128224 and International Publication WO 98/15226, and will does not be described specifically.

Thus the second arithmetic device 3 generates the second data representing a three-dimensional, anatomical image of the chest of the same subject in a vicinity of his/her heart and feeds the second data to display device 4 at the other input.

Display device 4 of FIG. 2 superimposes on a three-dimensional, anatomical image of a subject's chest based on the second data from the second arithmetic device 3 an image based on the first data from the first arithmetic device 2 and representing a three-dimensional, intramyocardial current density distribution.

Figure 7B:
FIGS. 7A and 7B show an example of a three-dimensional, anatomical image displayed on a display device 4.
Figure 7A:

FIGS. 7A and 7B each show a manner of displaying in real time a three-dimensional current density distribution superimposed on a three-dimensional, anatomical image displayed by display device 4. The figures show the current density distribution chronologically varying as time elapses.

FIGS. 7A and 7B each show a three-dimensional image obtained by interpolating approximately five tomographic images obtained for example by slicing a subject's chest at a pitch of five millimeters. An actually displayed image's depth is difficult to represent by drawing. In each of FIGS. 7A and 7B, a drawing configuring each image is represented by a plurality of superimposed drawings. As such, it can thus be determined to be a perspective, stereoscopic, anatomical image formed by combining a plurality of sliced images.

Note that FIGS. 7A and 7B each show a tomographic image with an upper portion corresponding to a front side of a human body and a lower portion to a back side thereof. Furthermore FIGS. 7A and 7B each show the tomographic image, as seen upward (at the legs).

In each of FIGS. 7A and 7B, a set of circles, as indicated by A, represents a three-dimensional current density distribution superimposed on a three-dimensional, anatomical image, and each circle's radius represents a magnitude of a current density. Alternatively, the magnitude of the current density can be represented by a tone of a specific color on a screen.

Figure 8:
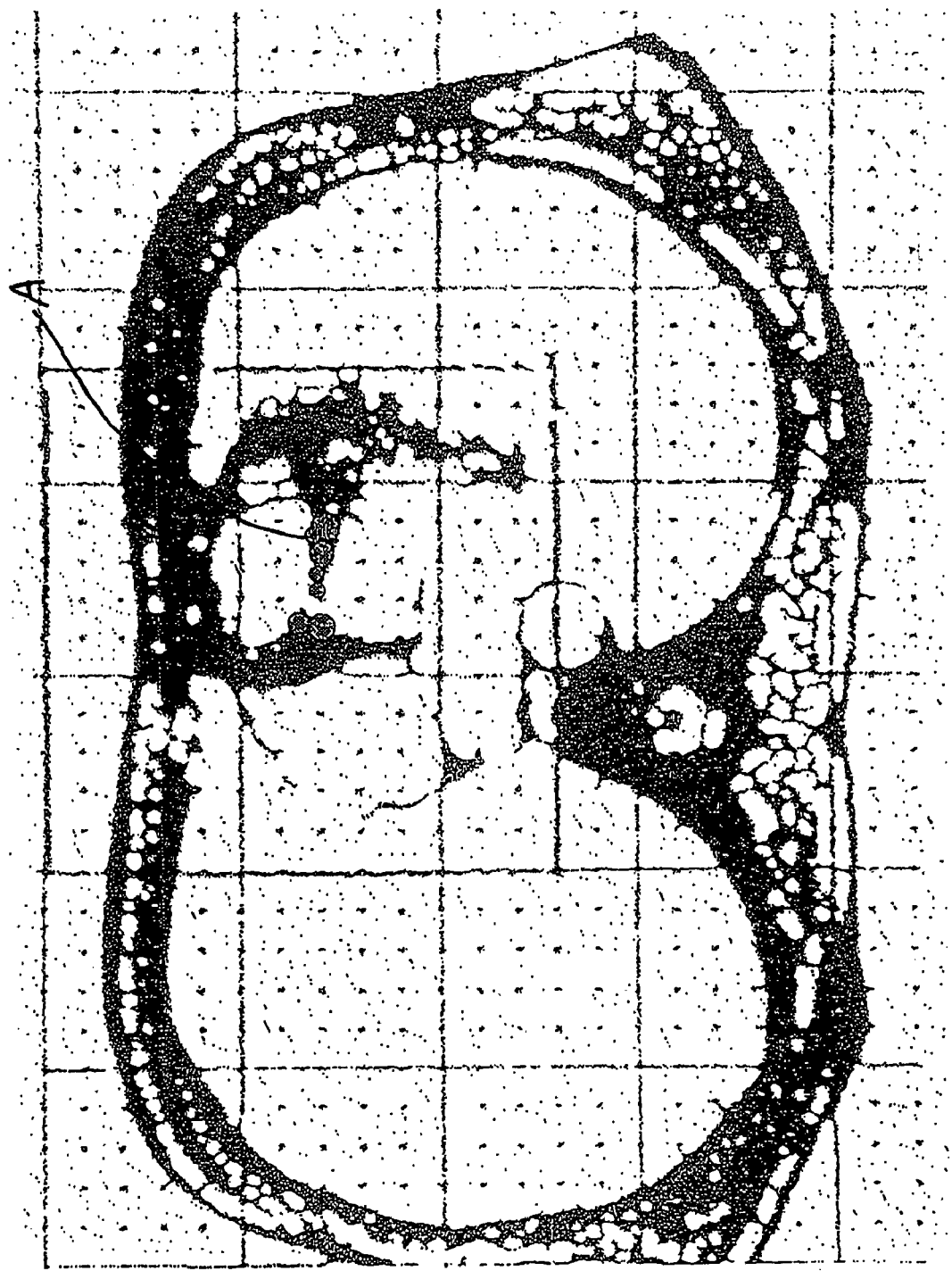
FIG. 8 tomographically shows a cross section of the three-dimensional, anatomical image shown in FIGS. 7A and 7B.

Furthermore, FIG. 8 displays an extracted tomographic image obtained at a depth of such a perspective, stereoscopic, anatomical image as shown in FIGS. 7A and 7B, with a set of circles, similarly as indicated by A, representing a current density distribution on the tomographic image.

The perspective, three-dimensional, anatomical image with the three-dimensional, intramyocardial current density distribution displayed thereon allows a doctor to correctly understand a relative, positional relationship of the intramyocardial current density distribution on the anatomical image. In particular, if a displayed current density distribution indicates abnormality, the doctor can correctly diagnose the location, size and geometry of a lesioned or viable part of myocardium.

Figure 9:
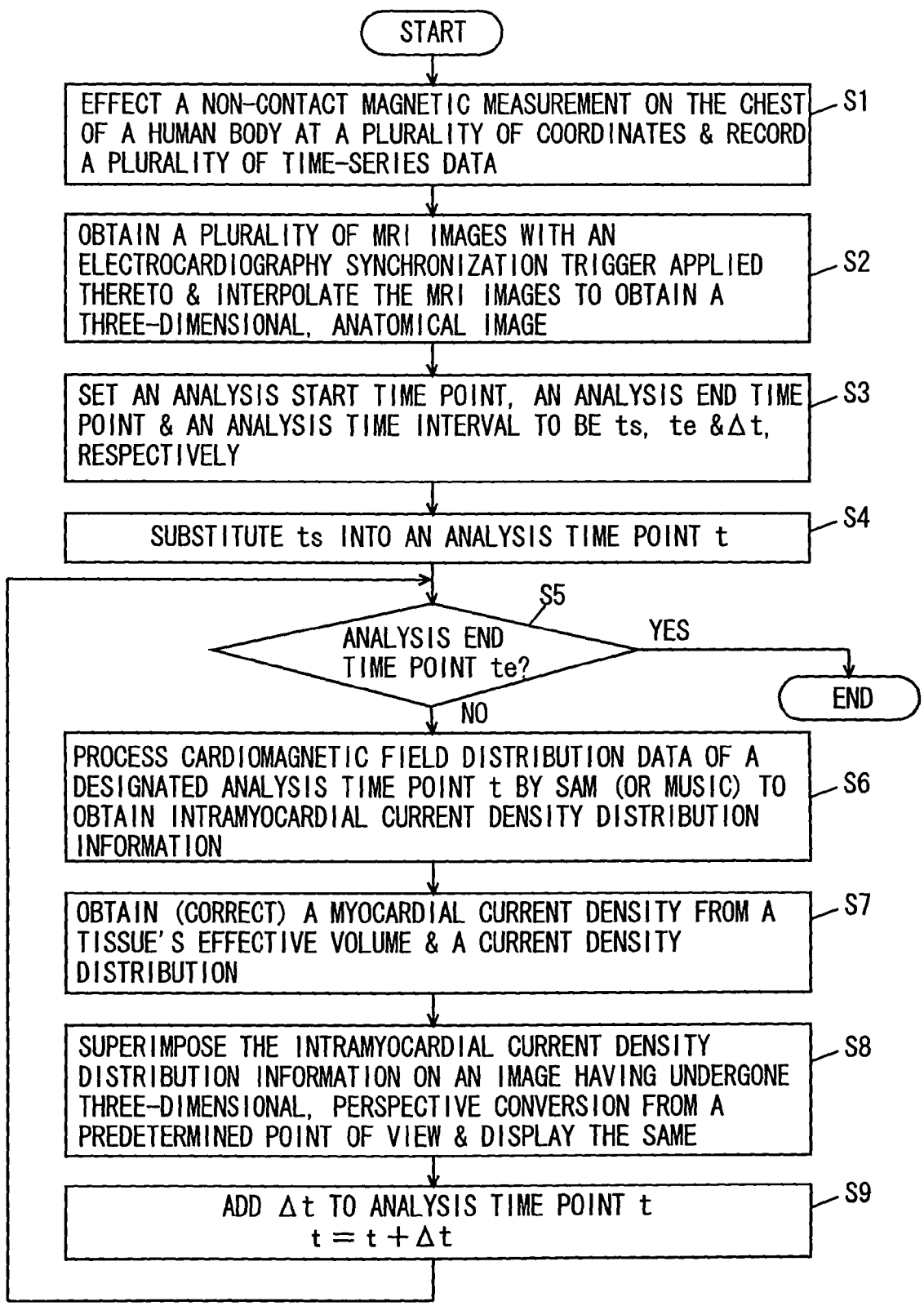
FIG. 9 is a flow chart for illustrating an operation of the apparatus employing a magnetic measurement to diagnose viable myocardium in the first embodiment.

FIG. 9 is a flow chart representing a method effected by the magnetocariogaphic diagnosis apparatus of the first embodiment to identify an intramyocardial current density distribution.

In FIG. 9 initially at step S1 magnetic field distribution measurement device 1 is used to provide non-contact magnetic measurement on the chest of a human body at a plurality of coordinates, generate a plurality of time series data, and record the data if necessary. Note that the arithmetic operation/operations performed by the first arithmetic device 2 using SAM or MUSIC as aforementioned is/are performable on time-series data supplied in real time.

Then at step S2 a plurality of MRI images taken with an electrocardiography synchronization trigger applied are interpolated by the second arithmetic device 3 (i.e., subjected to three-dimensional, perspective conversion from a predetermined point of view) to obtain a three-dimensional, anatomical image.

Then at step S3 an analysis start time point, an analysis end time point and an analysis time interval are set to be $t_s$, $t_e$ and $\Delta t$, respectively.

Then at step S4 analysis start time point $t_s$ is substituted into an analysis time point t to start an analysis. Then at step S5 until analysis time point t reaches analysis end time point $t_e$ the following process is effected.

More specifically at step S6 the first arithmetic device 2 uses SAM or MUSIC to process cardiomagnetic field distribution data corresponding to a designated analysis time point t and obtain intramyocardial current density distribution data.

Then, at step S7 an effective myocardial current density is obtained from an effective volume of a myocardial tissue and a calculated current density distribution. More specifically, the intramyocardial current density distribution data calculated at step S6 is corrected to be a value closer to the effective myocardial current distribution.

Then at step S8 display device 4 superimposes the intramyocardial current density on the anatomical image having been subjected to three-dimensional, perspective conversion from the predetermined point of view and displays the same.

Then at step S9 $\Delta t$ is added to analysis time point t.

Steps S6–S9 are repeated until a decision is made at step S5 that analysis time point t has reached analysis end time point $t_e$. When it reaches analysis end time point $t_e$ display device 4 terminates displaying the intramyocardial current density distribution superimposed on the anatomical image.

Note that, as has been described previously with reference to FIG. 1, information of a lesion at the part of myocardium of interest can be obtained from the information in database 5, as based on an intramyocardial current density distribution calculated by the first arithmetic device 2.

Figure 10:
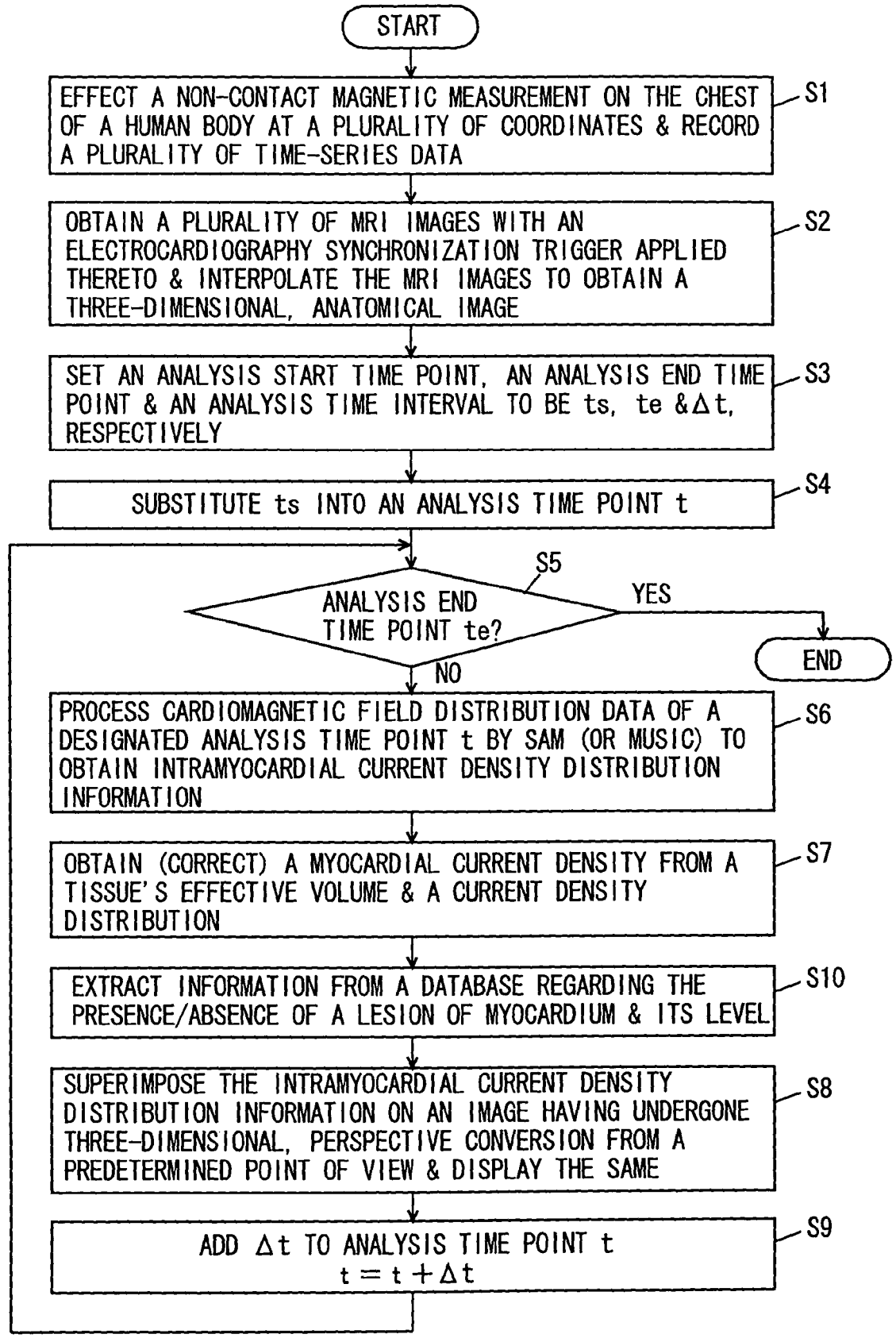
FIG. 10 is a flow chart for illustrating an operation of the apparatus employing a magnetic measurement to diagnose viable myocardium in the first embodiment in an exemplary variation.

FIG. 10 is a flow chart illustrating a process provided by an exemplary variation of the first embodiment and it is identical to the FIG. 9 flow chart, except the following:

More specifically, at step S10, from the information in database 5 regarding a myocardial lesion current that is based on the corrected myocardial current density obtained at step S7 the information of the presence/absence of a lesion in myocardium at the part of interest and the level of the lesion are extracted and simultaneously displayed on display device 4.

The first embodiment in a further exemplary variation will now be described with reference to FIGS. 11 and 12. In the first embodiment described above, on an anatomical image of a heart a current density distribution is three-dimensionally, visibly displayed. In this exemplary variation, right and left ventricles have myocardium divided into any plurality of regions based on an anatomical or functional factor of the heart and for each region a current density distribution is calculated.

More specifically, if an average of intramyocardial current densities can be obtained for each region and such averages can be compared to each other, whether an electric current flow satisfactorily or not can be determined for each region, which is a suitable material allowing doctors to determine whether a part of myocardium is a lesioned or viable part.

In dividing myocardium into regions, an anatomical characteristic of a heart is noted to divide right and left ventricles into any plurality of regions or an anatomical characteristic of a coronary artery is noted to divide a left ventricle into any plurality of regions. Alternatively, for example from an interventricular septum radially for every six degrees a density distribution is obtained to create a profile curve and furthermore create a functional representation of voltage and time of electrical conduction.

Figure 11:
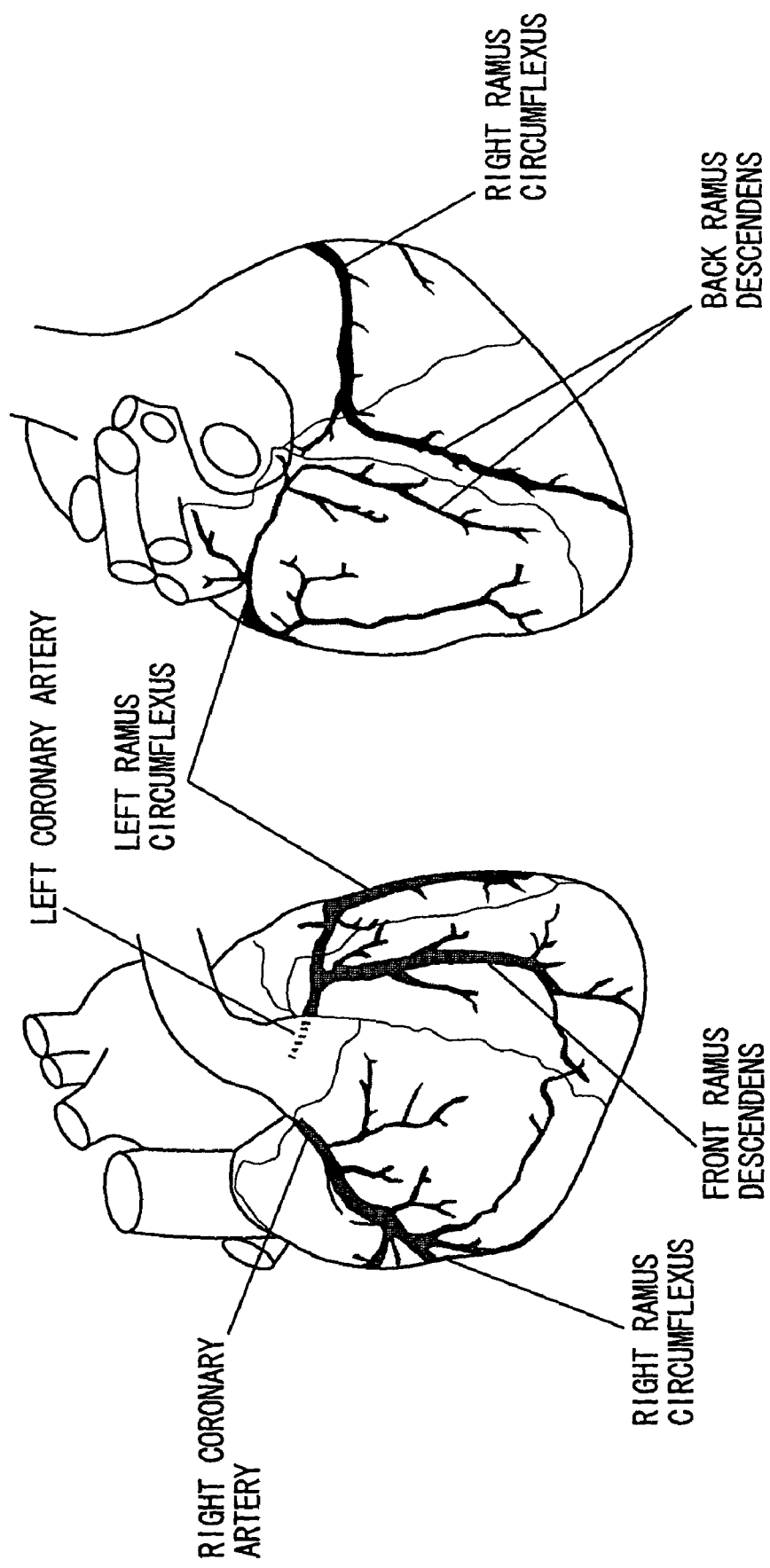
FIG. 11 schematically shows a manner of dividing a ventricle into regions.

FIG. 11 schematically shows a manner of dividing myocardium into regions when the position of a coronary artery is noted as an anatomical characteristic. In the FIG. 11 example, myocardium is divided into a region dominated by a front ramus descendens of a left coronary artery, that dominated by a left ramus circumflexus, and that dominated by a right coronary artery. For each of these regions a myocardial current density is calculated.

Figure 12:
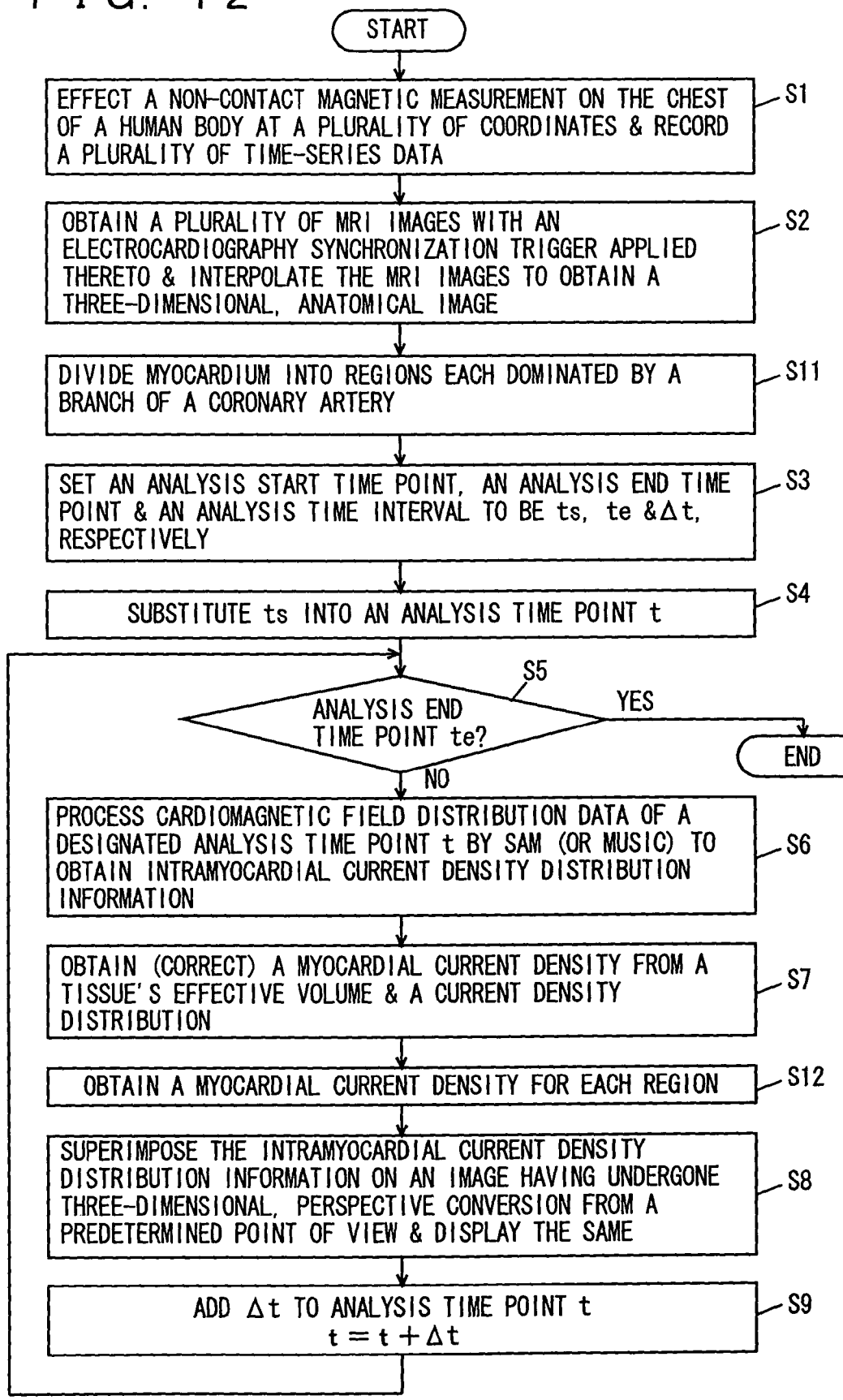
FIG. 12 is a flow chart for illustrating an operation of the present apparatus employing a magnetic measurement to diagnose viable myocardium in the first embodiment in another exemplary variation.

FIG. 12 is a flow chart of a process provided by a further exemplary variation of the first embodiment and it is identical to the FIG. 9 flow chart, except for the following:

More specifically, at step S11, in a three-dimensional, anatomical image obtained at step S2 myocardium is divided into regions each dominated by a branch of a coronary artery, as shown in FIG. 11. Then at step S12 from the myocardial current density calculated at step S7 a myocardial current density is obtained for each region provided at step S11. As such, in addition to three-dimensionally displaying a current density distribution in accordance with the first embodiment, a region of right and left ventricles that includes a lesioned part of myocardium can be readily, three-dimensionally identified.

Thus in accordance with the present invention in the first embodiment an image representing an intramyocardial current density distribution obtained from a SQUID magnetometer conducting a non-invasive magnetic measurement on a subject's chest that is superimposed on a three-dimensional, anatomical image can be displayed to allow doctors to identify safely, rapidly and with high precision, three-dimensionally identify the location, size, geometry and lesion level of a lesioned part of myocardium presenting an abnormal current density distribution or a viable part of myocardium to alleviate a burden on patients. Furthermore, a test can be conducted without using a radioactive isotope and hence continuously without an interval of days.

Furthermore, referring to an anatomical or functional factor to divide right and left ventricles into a plurality of regions and calculating a myocardial current density for each region allows three-dimensional diagnosis of a lesioned part of myocardium in the right and left ventricles and can thus facilitate considering approaches for treatment. In particular, if high frequency catheter cauterization is used to provide a treatment, it can previously, significantly narrow down a region to be electrophysiologically tested using a catheter and a test conducted while radioscopy is provided can be conducted in a significantly reduced period of time. Consequently, doctors and radiographers can avoid significantly large annual doses of x-ray exposure.

Furthermore, the database that is prepared to contain information used to determine a relationship between a current density and a myocardial lesion current allows a calculated current density distribution to be used to provide an accurate diagnosis of an electrophysiological property of a tissue of myocardium at the part of interest (e.g., an evaluation of viable myocardium, the presence/absence of a rejection after a heart transplant and the level of the rejection, and cardiomyopathy).

Second Embodiment

In the first embodiment, forming an anatomical image entails obtaining a large number of tomographic images of a subject and a test employing MRI, x-ray CT or the like is accordingly, previously conducted. This results in an increased number of tests and an increased burden on patients and also an obstacle to a treatment directly linked to a test.

The present invention in a second embodiment can provide a viable-myocardium diagnosis apparatus and analysis method employing a magnetic measurement capable of eliminating the formation of an anatomical image to conduct a reduced number of tests and carry out a diagnosis and a test such that they are directly linked.

Figure 13:
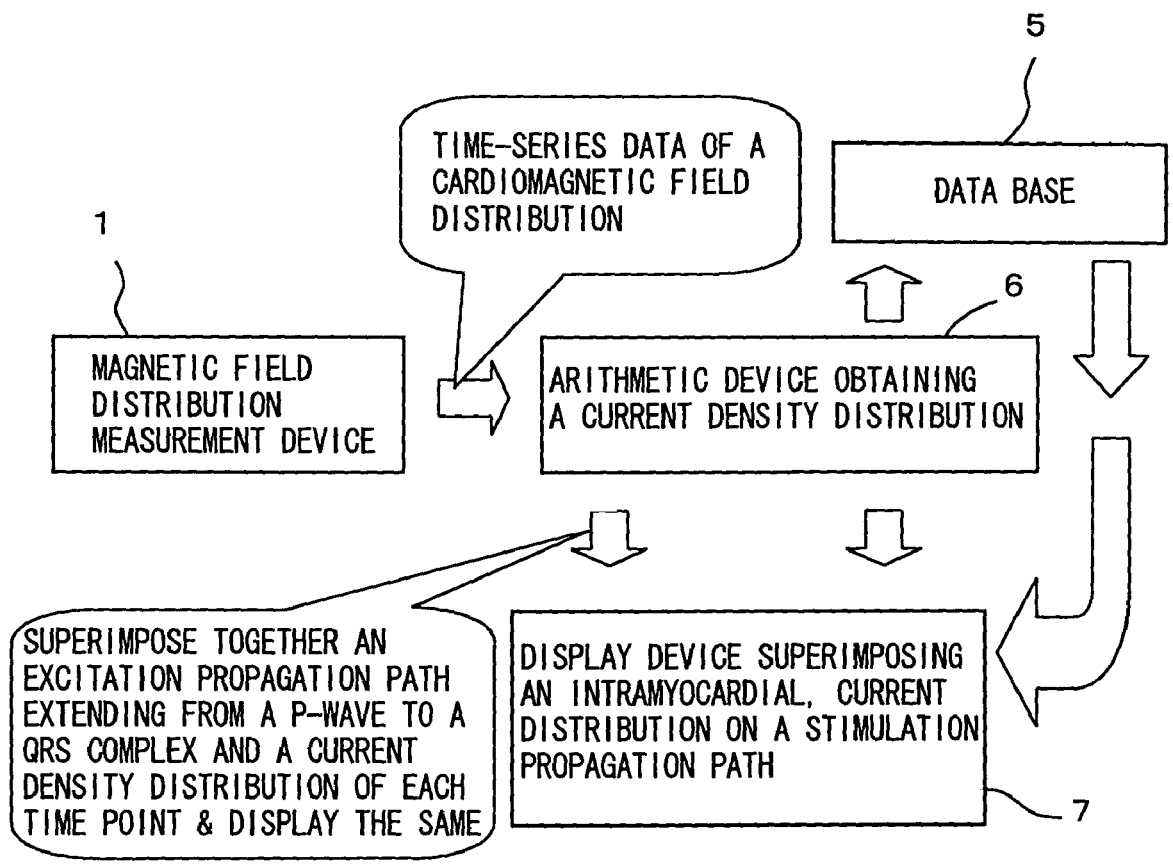
FIG. 13 is a functional block diagram schematically showing a configuration of an apparatus employing a magnetic measurement to diagnose viable myocardium in accordance with the present invention in a second embodiment.

FIG. 13 is a functional block diagram schematically showing a configuration of the viable-myocardium diagnosis apparatus employing magnetic measurement in the second embodiment.

With reference to FIG. 13, magnetic field distribution measurement device 1 will not be described as it has been described in the first embodiment.

Magnetic field distribution measurement apparatus 1 generates time-series, magnetic field distribution data and outputs the data to an arithmetic device 6 which in turn uses the received time-series, magnetic field distribution data and employs the aforementioned SAM, MUSIC or any other similar calculation technique to generate data representing an intramyocardial, three-dimensional current density distribution. Arithmetic device 6 then uses the generated three-dimensional current density distribution data to superimpose data representing an intracardiac excitation (stimulation) propagation path of a period corresponding to that from an electrocardiographically represented P wave to an electrocardiographically represented QRS complex and data representing a current density distribution on each other and outputs the same to display device 7.

Display device 7 superimposes an image representing the intramyocardial current density distribution represented by the data generated by arithmetic device 6, on a three-dimensional image of the excitation propagation path also obtained by arithmetic device 6 and corresponding to the period from the P wave to the QRS complex, and displays the same. Consequently, such an anatomical image as used in the first embodiment can be dispensed with to three-dimensionally identify an abnormal current density distribution in myocardium of a ventricle.

Note that as well as in the first embodiment, there is provided database 5 containing information used to determine a relationship between an intramyocardial current density distribution and a myocardial lesion current.

Figure 14:
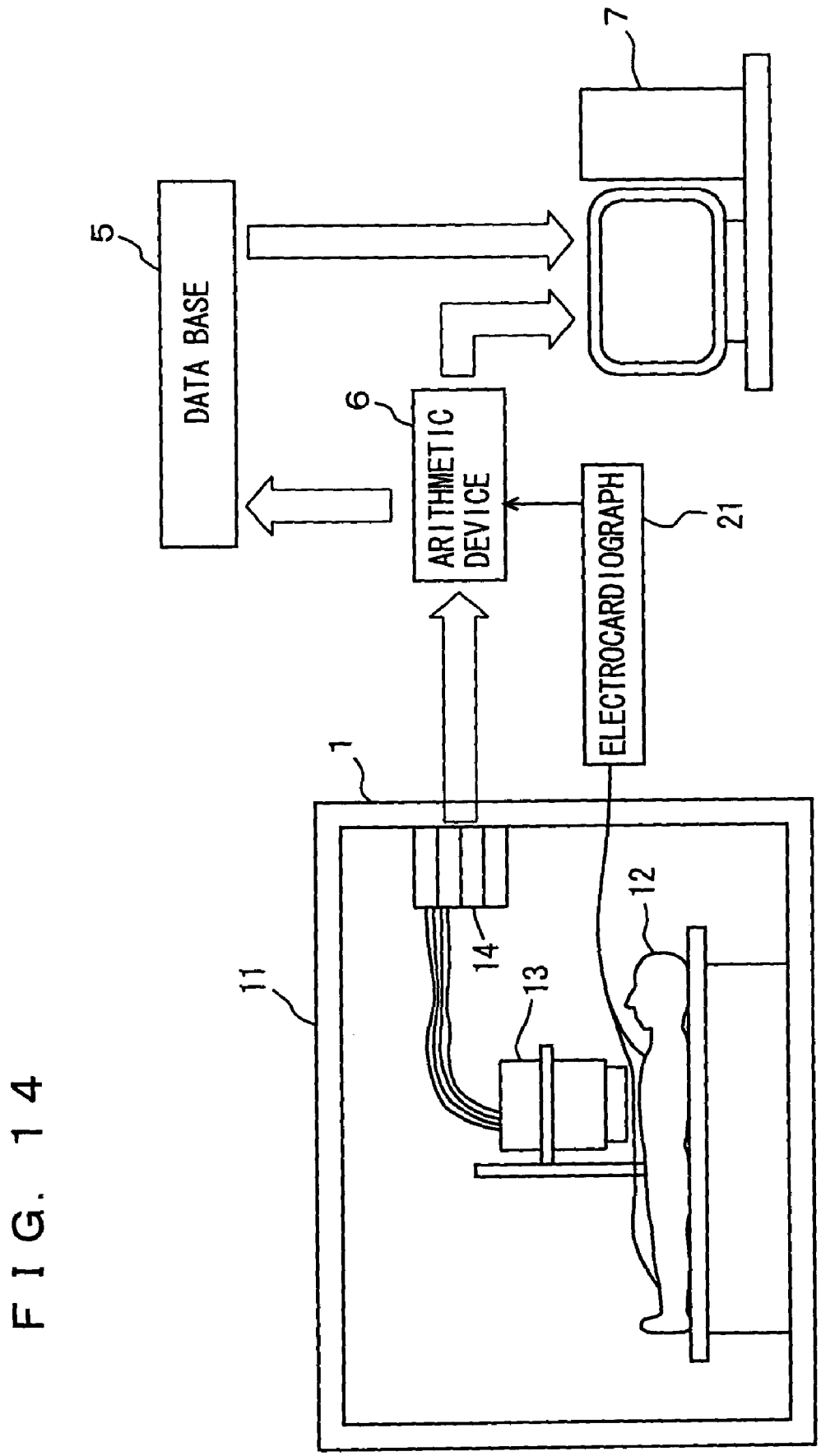
FIG. 14 is a block diagram more specifically showing the configuration of the apparatus employing a magnetic measurement to diagnose viable myocardium in the second embodiment shown in FIG. 13.

FIG. 14 is a block diagram more specifically showing the configuration of the viable-myocardium diagnosis apparatus employing magnetic measurement in the second embodiment shown in FIG. 13.

With reference to FIG. 14, magnetic field distribution measurement apparatus 1 will not be described as it is identical to that described with reference to FIGS. 2 and 3.

Magnetic field distribution measurement device 1 outputs time-series, magnetic field distribution data and outputs the data to arithmetic device 6 shown in FIG. 14. Arithmetic device 6 uses SAM, MUSIC or any other similar technique, as described with reference to FIG. 6, to convert the time-series, magnetic field distribution data to time-series, current density distribution data.

Subject 12 has his/her electrocardiogram recorded by an electrocardiograph 21 to allow measured electrocardiographic waveform data of subject 12 to be fed to arithmetic device 6.

Note herein that if the electrocardiographically represented waveform and a generated current density distribution can be correlated, the electrocardiogram and an event occurring in the heart can also be correlated.

Figure 15A:
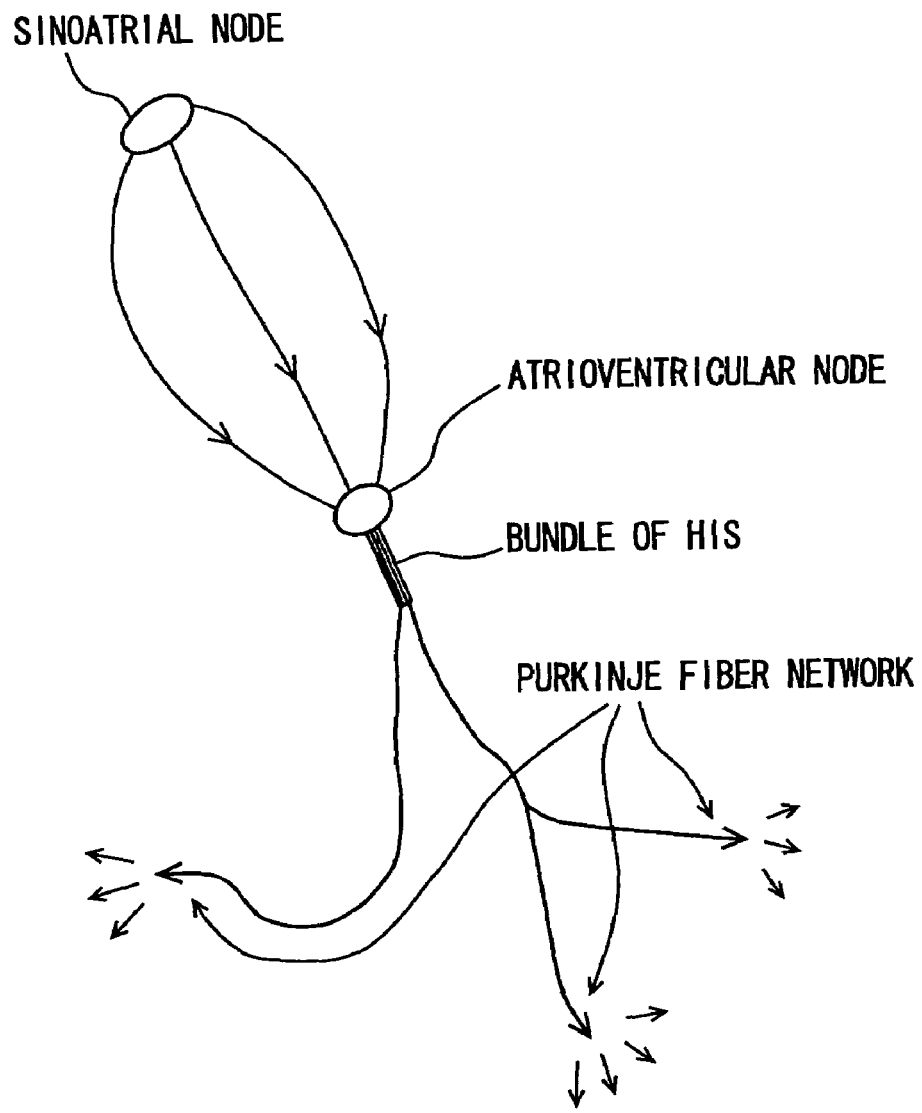
FIGS. 15A and 15B schematically show a normal stimulation propagation path in a heart and an electrocardiographically represented waveform.
Figure 15B:
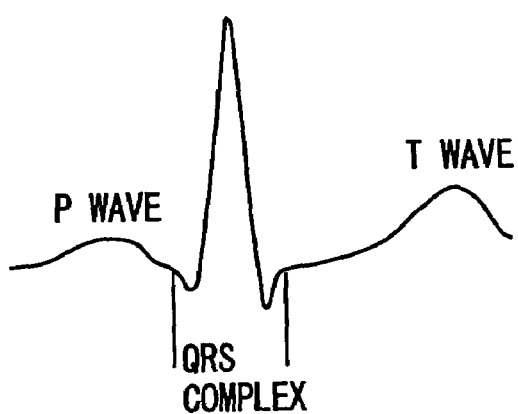

Reference will now be made to FIG. 15A schematically representing a normal stimulation propagation path in a heart and FIG. 15B representing an electrocardiographically represented waveform for a single heart beat.

With reference to FIGS. 15A and 15B, a sinoatrial node functions as a pacemaker determining a heart beat and it fires at predetermined intervals (a timing of a P wave of an electrocardiogram) to generate a pulse. This pulse is transmitted through a specific stimulation propagation path to an atrioventricular node and therein after a period of time elapses a pulse is transmitted through a bundle of His-Purkinje fiber network to an underlying a ventricle and myocardial contraction erupts. This propagation of a stimulation from the bundle of His to Purkinje fiber network corresponds to the period of the QRS complex in the electrocardiogram (an isovolumetric contraction time).

As such, by analyzing cardiomagnetism related to the period from the P wave to the QRS complex, i.e., an intramyocardial current density distribution, arithmetic device 5 generates image data representing a stimulation propagation path serving as a normal route, as shown in FIG. 15A.

An image of a stimulation propagation path, such as shown in FIG. 15A, can be used in place of the anatomical image used in the first embodiment, as a template displayed. More specifically, a three-dimensional, anatomical image such as described in the first embodiment can be dispensed with if a stimulation propagation path of a normal route, as shown in FIG. 15A, is displayed, since a lesioned part of myocardium present in a vicinity thereof that presents an abnormal current density distribution or a viable part of myocardium would be readily, anatomically correlated and its location, size and geometry would be identified by doctors.

Arithmetic device 6 shown in FIG. 14 generates data representing a generated current density distribution, superimposed on a displaying of a stimulation propagation circuit as a template, such as described above. As has been described previously, noting an image representing a current density distribution allows a lesioned or viable part of myocardium in a ventricle to be found, and such image data can be combined with the aforementioned template image data and fed to display device 7.

Display device 7 shown in FIG. 14 uses the data received from arithmetic device 6 to display an image representing a current density distribution, as superimposed on a normal stimulation propagation circuit serving as a template. Thus doctors can anatomically correlate a lesioned or viable part of myocardium.

Figure 16:
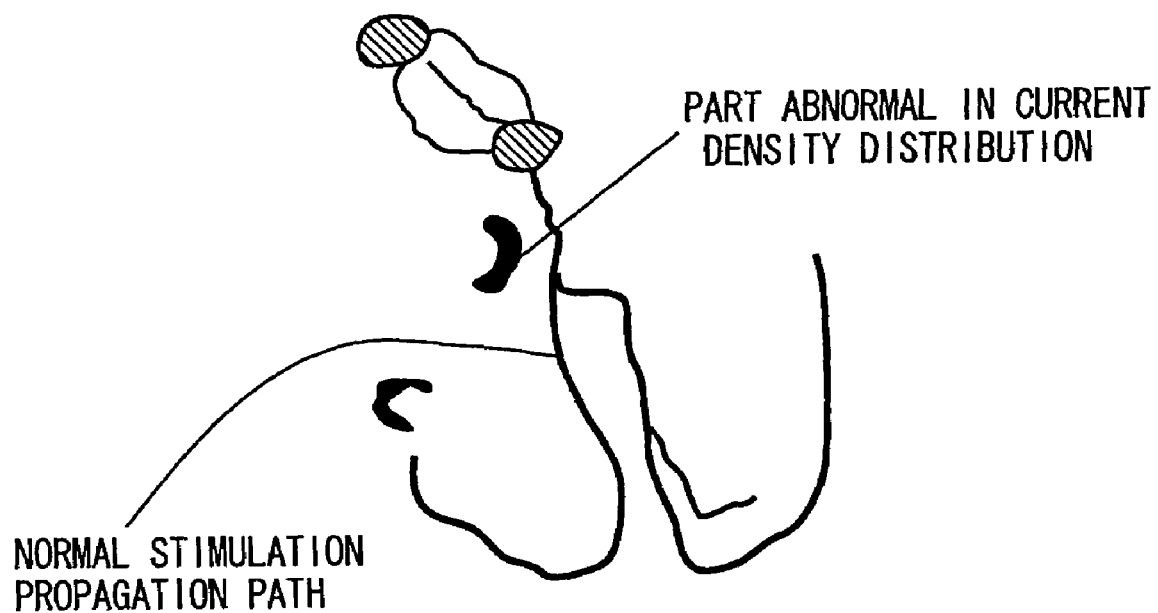
FIG. 16 shows an image of a normal stimulation propagation path and an abnormal current density distribution, as displayed by display device 7.

FIG. 16 exemplarily shows a screen actually displayed by display device 7. It displays an image of a part presenting an abnormal current density distribution, superimposed on a normal stimulation propagation circuit serving as a template.

A doctor would be able to use a positional relationship of the current density distribution relative to the normal stimulation propagation path serving as a template, as shown in FIG. 16, to readily provide an anatomical correlation and identify the location, size, geometry and level of a lesioned or viable part of myocardium in right and left ventricles.

Figure 17:
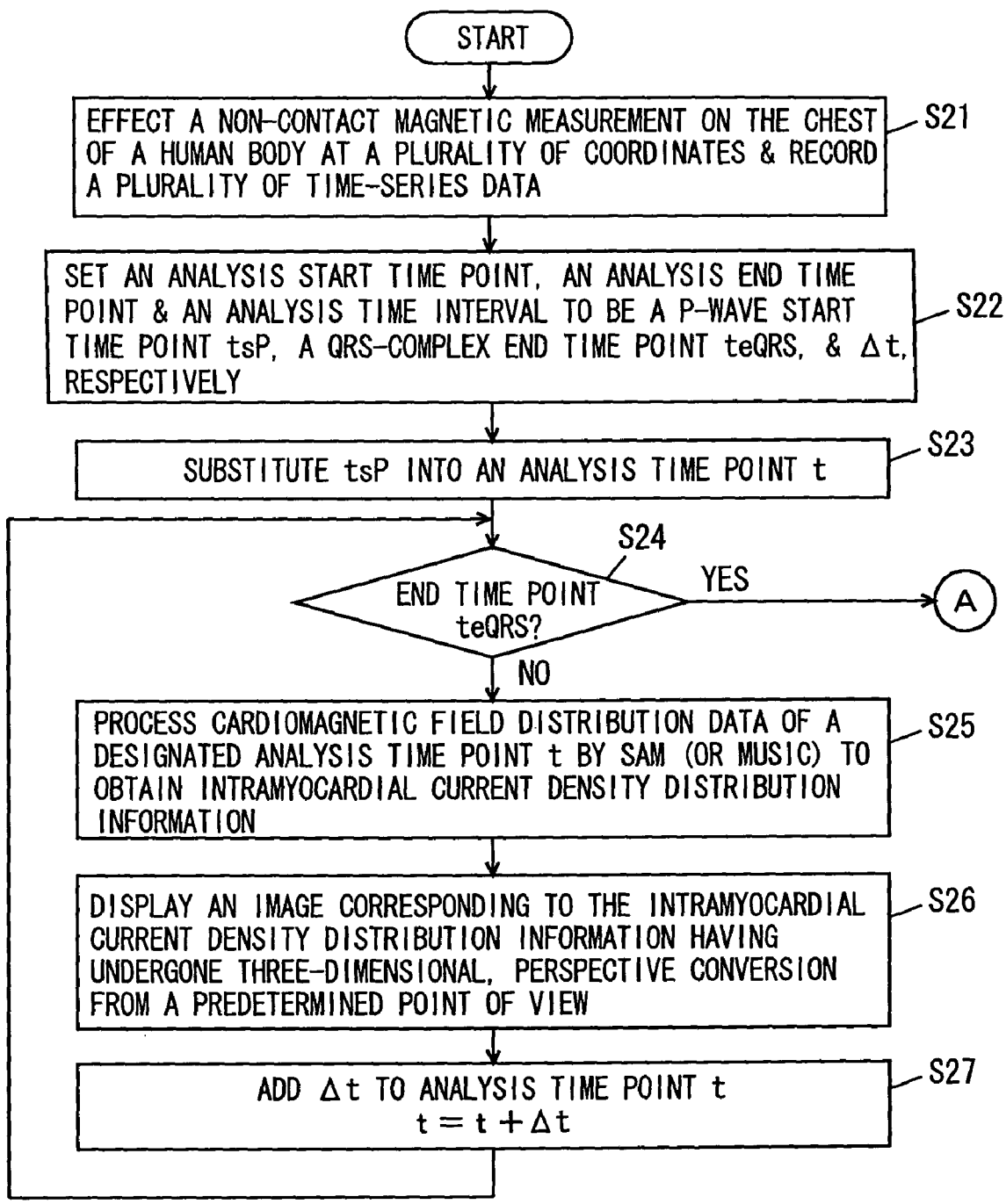
FIGS. 17 and 18 are a flow chart for illustrating first and second halves, respectively, of an operation of the apparatus employing a magnetic measurement to diagnose viable myocardium in the second embodiment.
Figure 18:
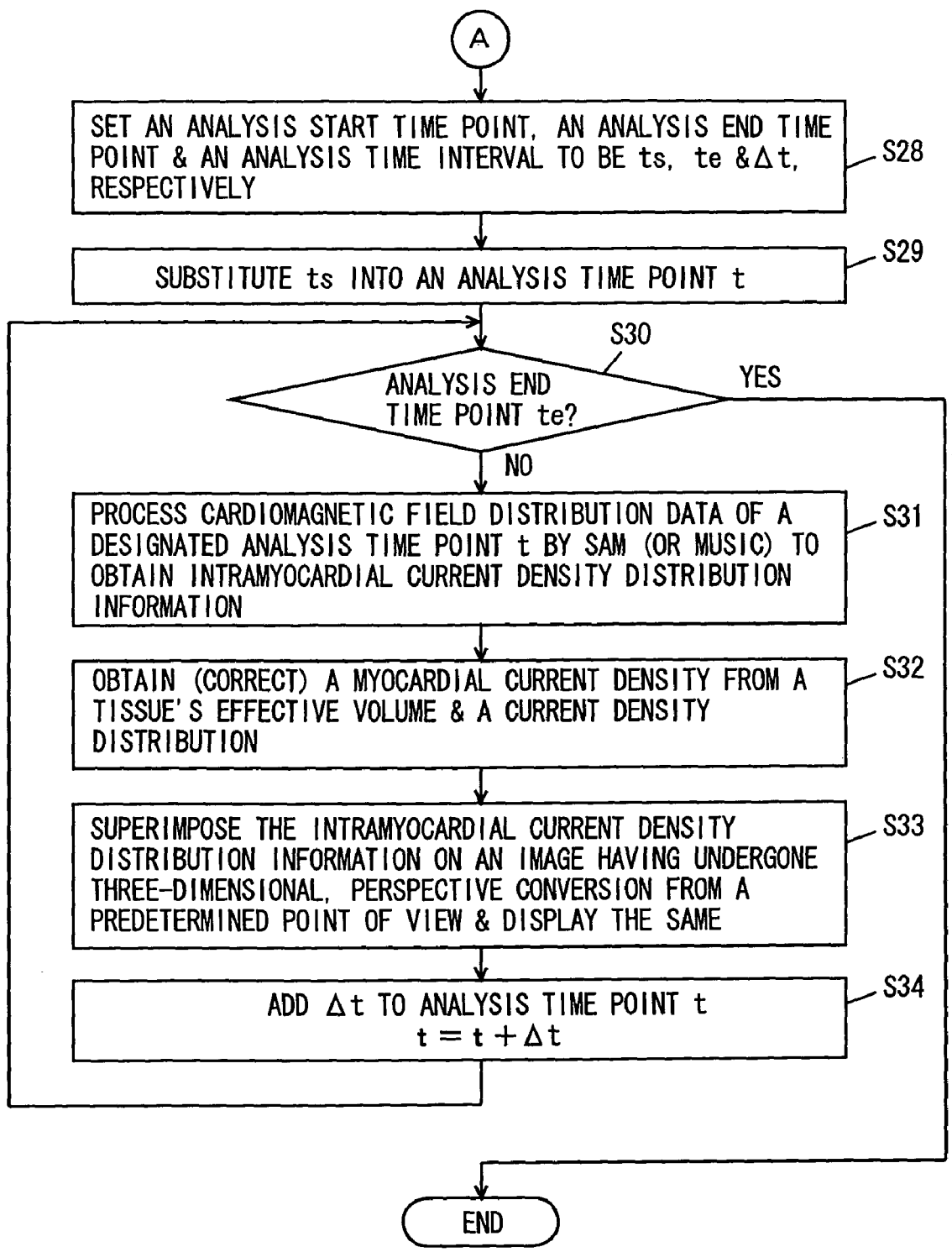

FIGS. 17 and 18 are a flow chart representing a method effected by the apparatus of the second embodiment to electrophysiologically analyze a viable myocardium.

Initially, with reference to FIG. 17, at step S21 magnetic field distribution measurement device 1 is used to provide a non-contact magnetic measurement on the chest of a human body at a plurality of coordinates to generate and record a plurality of time-series magnetic data.

Then at step S22 an analysis start time point is set to correspond to an electrocardiographically represented P-wave start time point $t_{sP}$, an analysis end time point to an electrocardiographically represented QRS-complex end time point $t_{eQRS}$, and an analysis time interval to $\Delta t$.

Then at step S23 time point $t_{sP}$ is substituted into analysis time point t.

Then at step S24 until an analysis time reaches time point $t_{eQRS}$ the following steps S25–S27 are repeated.

More specifically at step S25 arithmetic device 6 uses SAM or MUSIC to process cardiomagnetic field distribution data of a designated analysis time point t to generate intramyocardial current density distribution data.

Then at step S26 the intramyocardial current density distribution data having been subjected to three-dimensional, perspective conversion from a predetermined point of view is displayed in an image.

Then at step S27 $\Delta t$ is added to analysis time point t and the process returns to step S24 and a decision is made as to whether time point $t_{eQRS}$ has been reached. If so then it means that there has been obtained image data representing a stimulation propagation path corresponding to a normal route, as shown in FIG. 15A, as corresponding in an electrocardiographically represented waveform to the period from the P wave to the QRS complex.

Then the process proceeds with step S28, shown in FIG. 18, and an analysis start time point, an analysis end time point and an analysis time interval are set to be $t_s$, $t_e$ and $\Delta t$, respectively.

Then at step S29 analysis start time point $t_s$ is substituted into analysis time point t.

Then at step S30 until a decision is made that analysis time point t has reached analysis end time point $t_e$ the following steps S31–S34 are effected.

More specifically, at step S31 arithmetic device 6 uses SAM or MUSIC to process cardiomagnetic field distribution data of a designated analysis time point t to generate intramyocardial current density distribution data.

Then at step S32 an effective myocardial current density is obtained from the effective volume of a myocardial tissue and a calculated current density distribution. More specifically, the current density distribution data calculated at step S31 is corrected to have a value closer to the effective myocardial current density.

Then at step S33 the intramyocardial current density data is superimposed on an image of a normal stimulation propagation circuit having been subjected to three-dimensional, perspective conversion from a predetermined point of view, and it is thus displayed.

Furthermore at step S34 $\Delta t$ is added to analysis time point t and the process returns to step S30 and a decision is made as to whether analysis end time point $t_e$ has been reached. Thus, data representing the intramyocardial current density distribution is superimposed on an image of a normal stimulation propagation path (FIG. 15A) obtained through the FIG. 17 flow chart, and it is thus displayed.

Note that as well as in the first embodiment, from database 5 of FIG. 13 information can be obtained regarding a lesion in myocardium at a lesioned part.

Figure 19:
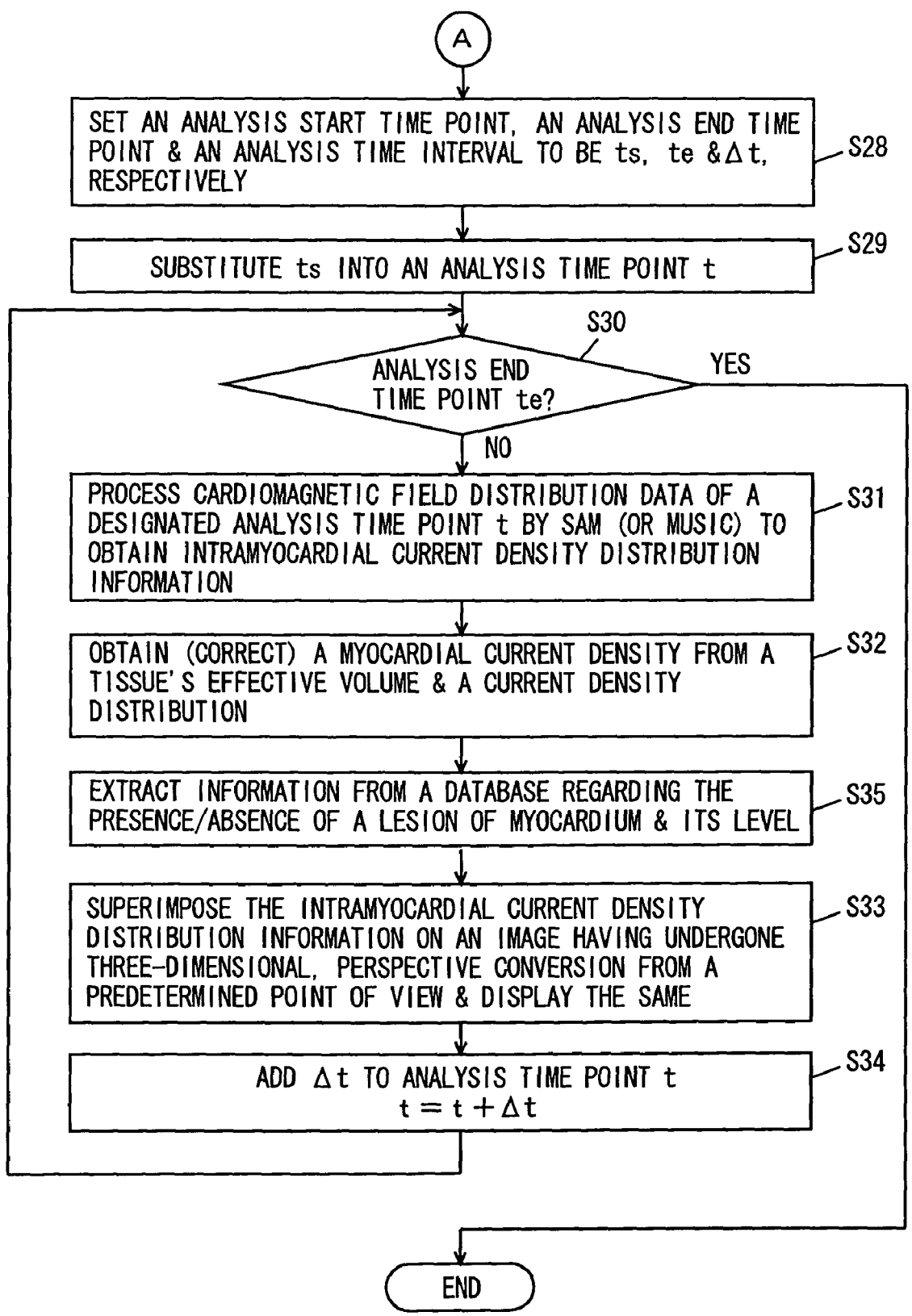
FIG. 19 is a flow chart for illustrating a second half of an operation of the apparatus employing a magnetic measurement to diagnose viable myocardium in the second embodiment in an exemplary variation.

FIG. 19 is a flow chart of a process of an exemplary variation of the second embodiment and it is identical to the FIG. 18 flow chart, except the following:

More specifically, at step S35, from the information in database 5 regarding a myocardial lesion current that is based on the corrected myocardial current distribution obtained at step S32 the information of the presence/absence of a lesion in myocardium at the part of interest and the level of the lesion are extracted and simultaneously displayed on display device 7.

Then, as well as in the first embodiment, in the present embodiment right and left ventricles may also have their myocardium divided into any plurality of regions based on an anatomical or functional factor of the heart and for each region a current density distribution may be calculated. The myocardium is divided into regions in the manner as described in the first embodiment.

Figure 20:
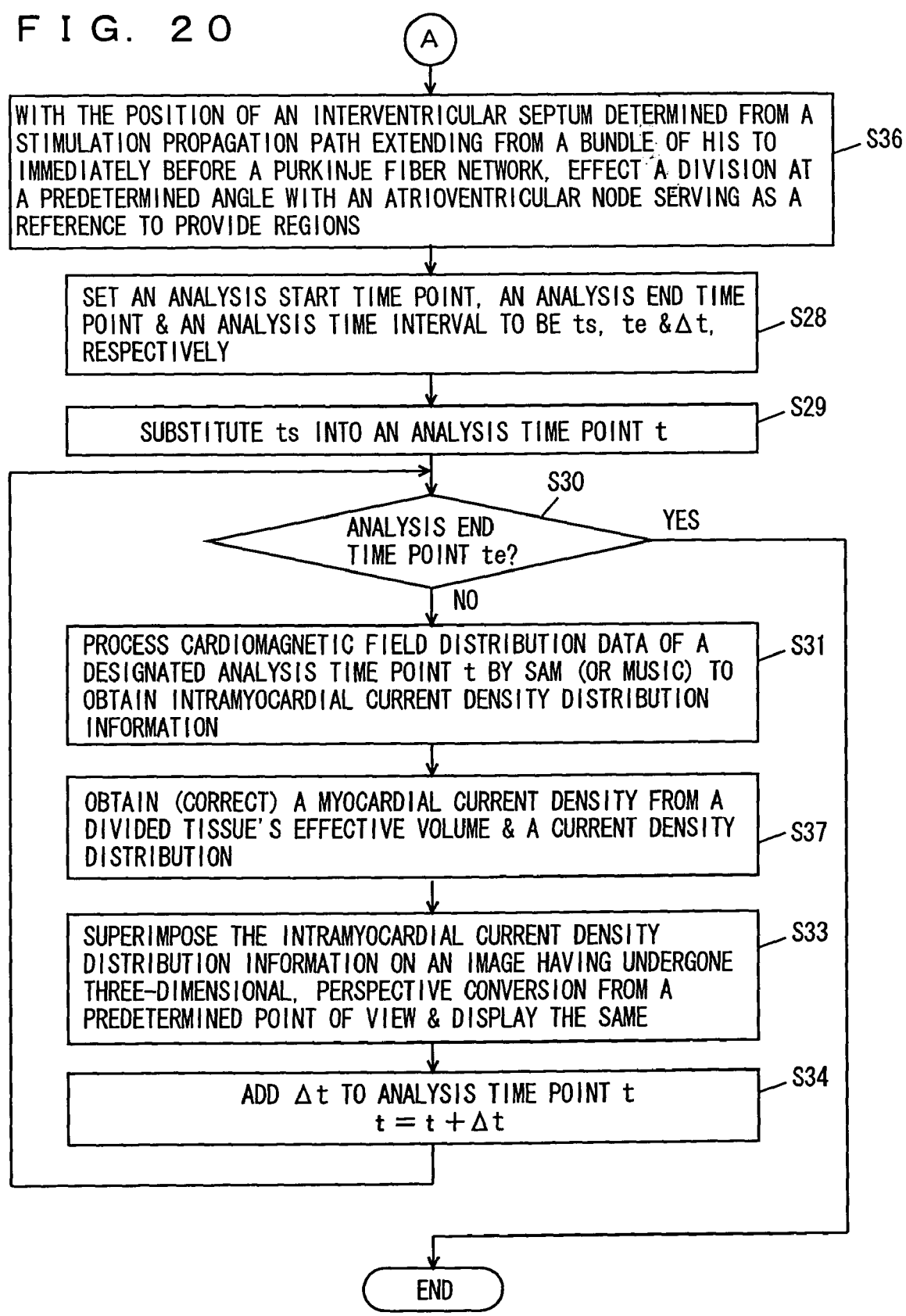
FIG. 20 is a flow chart for illustrating a second half of an operation of the apparatus employing a magnetic measurement to diagnose viable myocardium in the second embodiment in another exemplary variation.

FIG. 20 is a flow chart of a process provided by the variation of the second embodiment, as described above, and it is identical to the FIG. 18 flow chart.

More specifically, at step S36 the position of an interventricular septum is clarified from information of a stimulation propagation path extending from a bundle of His to immediately before a Purkinje fiber network that is obtained by arithmetic device 6. Accordingly, a ventricle is divided into a plurality of regions at a predetermined angle with an atrioventricular node serving as a reference. Then, at step S37, from the effective volume and current density distribution of each region of a thus divided tissue a myocardial current density calculated for each region can be obtained.

Thus in accordance with the present invention in the second embodiment an image representing an intramyocardial current density distribution obtained from a SQUID magnetometer obtaining a non-invasive magnetic measurement on a subject's chest that is superimposed on a normal stimulation propagation path serving as a template can be displayed to be eliminate the necessity of superimposing it on a different, anatomical image to allow doctors to safely, rapidly and with high precision, three-dimensionally identify the location, size, geometry and level of a lesioned part of myocardium exhibiting an abnormal current density distribution, or a viable part of myocardium. Electrophysiological function in the myocardium can thus be non-invasively, rapidly and safely tested. An invasion on patients can thus significantly be alleviated. Furthermore, a previous test conducted to obtain an anatomical image can be eliminated.

Furthermore, a test can be conducted without using a radioactive isotope. This can reduce the cost and the test can be conducted continuously without an interval of days.

Furthermore, referring to an anatomical or functional factor to divide right and left ventricles into a plurality of regions and calculating a myocardial current density for each region allows three-dimensional diagnosis of a lesioned part of myocardium in the right and left ventricles and can thus facilitate considering approaches for treatment. In particular, if high frequency catheter cauterization is used to provide a treatment, it can previously, significantly narrow down a region to be electrophysiologically tested using a catheter and a test conducted while radioscopy is provided can be conducted in a significantly reduced period of time. Consequently, doctors and radiographers can avoid significantly large annual doses of x-ray exposure.

Furthermore, the database that is used to determine a relationship between a current density and a myocardial lesion current allows an accurate diagnosis of an electrophysiological function of myocardium (e.g., an evaluation of viable myocardium, the presence/absence of a rejection after a heart transplant and the level the rejection, and cardiomyopathy).

Thus in the present invention an intramyocardial current density distribution obtained from a non-invasive magnetic measurement performed on a patient's chest can be visibly displayed on a three-dimensional, anatomical image to allow three-dimensional identification of the location, size, geometry and level of a lesioned part of myocardium exhibiting an abnormal current density distribution or a viable part of myocardium. This allows non-invasive diagnosis of the lesioned or viable part of myocardium. As such, a test can be conducted rapidly and safely without imposing a significant burden on patients. Furthermore, a test can be conducted without using a radioactive isotope. As such, it can be conducted continuously, which can effectively reduce the cost.

Furthermore, referring to an anatomical or functional factor to divide right and left ventricles into a plurality of regions and calculating a myocardial current density for each region allows three-dimensional diagnosis of a lesioned or viable part of myocardium. In particular, if high frequency catheter cauterization is used to provide a treatment, it can previously, significantly narrow down a region to be electrophysiologically tested using a catheter. Consequently, doctors and radiographers can effectively avoid significantly large doses of x-ray exposure.

Furthermore, the database that is prepared to contain information used to determine a relationship between a current density and a myocardial lesion current uniquely effectively allows an accurate diagnosis of an electrophysiological property of a tissue of myocardium.

In accordance with the present invention, in still another aspect, superimposing a current density distribution on a normal stimulation propagation circuit in the same subject extending from a sinoatrial node to a bundle of His-a Purkinje fiber network, and three-dimensionally displaying the same can eliminate the necessity of obtaining an anatomical image to three-dimensionally identify the location, size, geometry and level of a lesioned or viable part of myocardium in a ventricle. In other words, a test conducted to obtain an anatomical image can be eliminated to effectively provide a more cost-effective diagnosis.

INDUSTRIAL APPLICABILITY

Thus the present invention can provide a viable-myocardium diagnosis apparatus and analysis method employing a magnetic measurement, capable of three-dimensionally identifying the location, size, geometry and level of a lesioned part of myocardium exhibiting an abnormal current density distribution or a viable part of myocardium. It is thus useful in non-invasive diagnosis of a lesioned or viable part of myocardium and furthermore in a treatment employing high frequency catheter cauterization.

The invention claimed is:

1. An apparatus employing a magnetic measurement to diagnose viable myocardium, comprising:
a magnetic field distribution measurement device performing a non-contact magnetic measurement on a subject's chest at a plurality of coordinates to obtain a plurality of time-series magnetic data corresponding to said plurality of coordinates, and also using said plurality of time-series magnetic data to generate time-series, magnetic field distribution data on said chest;
a first arithmetic device using said generated time-series, magnetic field distribution data to generate time-series, intramyocardial current density distribution data of said subject;
a second arithmetic device processing separately provided, tomographic, thoracic data of said subject to generate data representative of an anatomical image;
a display device displaying an image of said intramyocardial, current density distribution represented by said data generated by said first arithmetic device, as superimposed on said anatomical image represented by said data generated by said second arithmetic device, thereby capable of three-dimensionally identifying a lesioned part of myocardium presenting an abnormal current density distribution or a physiologically viable part of myocardium; and
a database containing information used to determine a relationship between an intramyocardial current density represented by data generated by said first arithmetic device and a myocardial lesion current.

2. An apparatus employing a magnetic measurement to diagnose viable myocardium, comprising:
a magnetism distribution measurement device performing a non-contact magnetic measurement on a subject's chest at a plurality of coordinates to obtain a plurality of time-series magnetic data corresponding to said plurality of coordinates, and also using said plurality of time-series magnetic data to generate time-series magnetic field distribution data on said chest;
an arithmetic device using said generated time-series, magnetism distribution data to generate time-series, intramyocardial current density distribution data of said subject; and
a display device using the data generated by said arithmetic device to superimpose together an image representing a stimulation propagation path of said subject extending from a sinoatrial node to a bundle of His-Purkinje fiber network and an image representing an intramyocardial current density distribution and display said images, thereby capable of three-dimensionally identifying a lesioned part of myocardium presenting an abnormal current density distribution or a physiologically viable part of myocardium.

3. The apparatus of claim 2, wherein said arithmetic device operates based on an anatomical or functional factor to divide right and left ventricles into any plurality of regions and generate time-series data of an intramyocardial current density distribution for each said region to allow a lesioned part of myocardium in the right and left ventricles to be three-dimensionally identified.

4. The apparatus of claim 2, further comprising a database containing information used to determine a relationship between an intramyocardial current density represented by data generated by said arithmetic device and a myocardial lesion current.

5. A method employing a magnetic measurement to analyze viable myocardium, comprising the steps of:
performing a non-contact magnetic measurement on a subject's chest at a plurality of coordinates to obtain a plurality of time-series magnetic data corresponding to said plurality of coordinates and used to generate time-series, magnetic field distribution data of said chest and generating first data corresponding to time-series, intramyocardial current density distribution data of said subject from the generated time-series magnetic field distribution data;

processing separately fed, tomographic, thoracic image data of said subject to generate second data representative of an anatomical image; and displaying an image of said intramyocardial current density distribution represented by said first data, as superimposed on said anatomical image represented by said second data, to allow three-dimensional identification of a lesioned part of myocardium presenting an abnormal current density distribution or a physiologically viable part of myocardium.

6. The method of claim 5, wherein the step of generating the first data divides right and left ventricles into any plurality of regions based on an anatomical or functional factor and generates time-series data of an intramyocardial current density distribution for each said region to allow a lesioned part of myocardium in the right and left ventricles to be three-dimensionally identified.

7. The method of claim 5, wherein said intramyocardial current density distribution is obtained through synthetic aperture magnetometry (SAM) or multiple signal classification (MUSIC).

8. A method employing a magnetic measurement to analyze viable myocardium, comprising the steps of:

performing a non-contact magnetic measurement on a subject's chest at a plurality of coordinates to obtain a plurality of time-series magnetic data corresponding to said plurality of coordinates and used to generate time-series, magnetic field distribution data of said chest and generating first data corresponding to time-series, intramyocardial current density distribution data of said subject from the generated time-series magnetic field distribution data;

processing separately fed, tomographic, thoracic image data of said subject to generate second data representative of an anatomical image;

displaying an image of said intramyocardial current density distribution represented by said first data, as superimposed on said anatomical image represented by said second data, to allow three-dimensional identification of a lesioned part of myocardium presenting an abnormal current density distribution or a physiologically viable part of myocardium, and determining from information indicating a relationship between an intramyocardial current density represented by said first data and a myocardial lesion current whether said three-dimensionally identified part is a lesioned or viable part of myocardium.

9. A method employing a magnetic measurement to analyze viable myocardium, comprising the steps of:

performing a non-contact magnetic measurement on a subject's chest at a plurality of coordinates to obtain a plurality of time-series magnetism data corresponding to said plurality of coordinates and used to generate time-series magnetism distribution data of said chest and generating time-series, intramyocardial current density distribution data of said subject from the generated time-series magnetism distribution data; and using said generated data to superimpose together an image representing a stimulation propagation path of said subject extending from a sinoatrial node to a bundle of His-a Purkinje fiber network and an image representing an intramyocardial current density distribution and displaying said images to allow three-dimensional identification of a lesioned part of myocardium presenting an abnormal current density distribution or a physiologically viable part of myocardium.

10. The method of claim 9, wherein the step of generating data divides right and left ventricles into any plurality of regions based on an anatomical or functional factor and generates time-series data of an intramyocardial current density distribution for each said region to allow a lesioned part of myocardium in the right and left ventricles to be three-dimensionally identified.

11. The method of claim 9, further comprising the step of determining from information indicating a relationship between an intramyocardial current density represented by said data and a myocardial lesion current whether said three-dimensionally identified part is a lesioned or viable part of myocardium.

* * * * *